US008895247B2

(12) United States Patent
Jenkins et al.

(10) Patent No.: US 8,895,247 B2
(45) Date of Patent: Nov. 25, 2014

(54) METHOD FOR DETECTION OF HUMAN PAPILLOMAVIRUS (HPV) TYPE

(75) Inventors: Andrew Jenkins, Skien (NO); Anne-Gry Allum, Svarstad (NO); Linda Strand, Porsgrunn (NO)

(73) Assignee: Allum-Jenkins AS, Skien (NO)

( * ) Notice: Subject to any disclaimer, the term of this patent is extended or adjusted under 35 U.S.C. 154(b) by 190 days.

(21) Appl. No.: 13/266,943

(22) PCT Filed: Apr. 22, 2010

(86) PCT No.: PCT/NO2010/000147
§ 371 (c)(1),
(2), (4) Date: Dec. 28, 2011

(87) PCT Pub. No.: WO2010/126375
PCT Pub. Date: Nov. 4, 2010

(65) Prior Publication Data
US 2012/0100528 A1    Apr. 26, 2012

(30) Foreign Application Priority Data

Apr. 30, 2009 (NO) .................................. 20091733

(51) Int. Cl.
*C12Q 1/68* (2006.01)
*C07H 21/04* (2006.01)
*C12Q 1/70* (2006.01)

(52) U.S. Cl.
CPC .............. *C12Q 1/708* (2013.01); *C12Q 1/6851* (2013.01)
USPC ...................... 435/6.12; 536/24.32; 536/24.33

(58) Field of Classification Search
USPC ................... 435/6.12, 810; 536/24.33, 24.32
See application file for complete search history.

(56) References Cited

U.S. PATENT DOCUMENTS

| 5,484,699 A | 1/1996 | Bouma et al. |
| 5,821,087 A * | 10/1998 | Lowe et al. .................. 435/69.3 |
| 6,218,104 B1 * | 4/2001 | Morris et al. ..................... 435/5 |
| 7,553,955 B2 * | 6/2009 | El-Deiry et al. ............. 536/24.3 |

FOREIGN PATENT DOCUMENTS

| DE | 199 03 056 | 8/2000 |
| WO | 99/14377 | 3/1999 |
| WO | 2006/077102 | 7/2006 |
| WO | 2007/130519 | 11/2007 |
| WO | 2008/096177 | 8/2008 |
| WO | 2010/126375 | 11/2010 |

OTHER PUBLICATIONS

Lowe et al. Nucleic acid research, 1990, vol. 18(7), p. 1757-1761.*
The nucleic acid sequence search reports (AC: AR048282, AAT29881, ATT29903).*
International Search Report issued Aug. 17, 2010 in corresponding International Application No. PCT/NO2010/000147.
English translation of International Preliminary Report on Patentability issued Jun. 28, 2011 in PCT/NO2010/000147.
Norwegian Search Report issued Nov. 19, 2009 in corresponding Norwegian Application No. 20091733.
Csaba Jeney, et al., "Detection and typing of 46 genital human papillomaviruses by the L1F/L1R primer system based multiplex PCR and hybridization", Journal of Virological Methods, 2007, vol. 140, pp. 32-42.
Examination Report issued May 7, 2012 in corresponding New Zealand Application No. 596252.

* cited by examiner

*Primary Examiner* — Kenneth R. Horlick
*Assistant Examiner* — Joyce Tung
(74) *Attorney, Agent, or Firm* — Wenderoth, Lind & Ponack LLP

(57) ABSTRACT

The present invention describes a method for detection of human papillomavirus (HPV) types and a kit for detection of said HPV types.

6 Claims, 17 Drawing Sheets

Cycle Number

Figure 1:
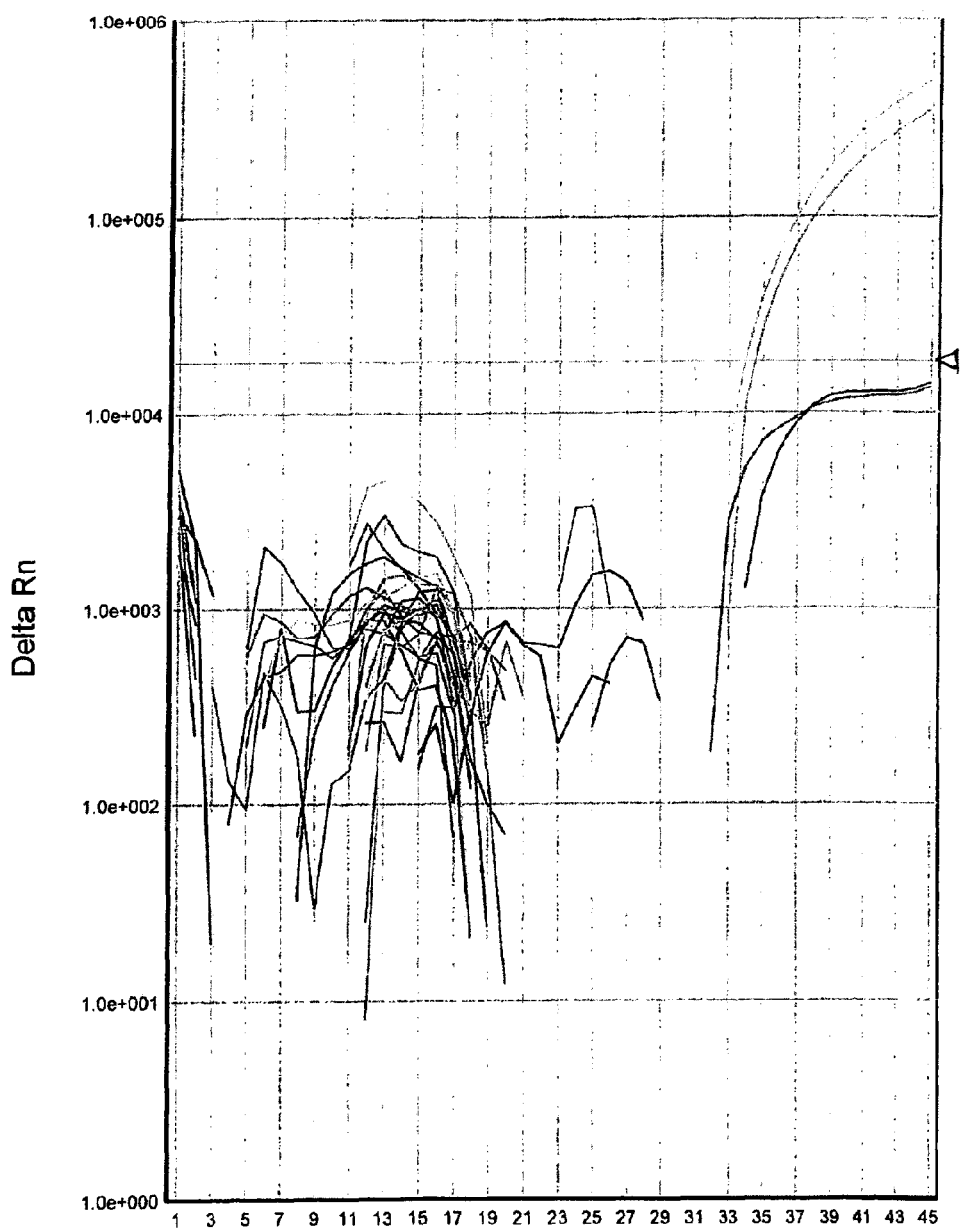

Selected Detector: PT16(6); Start: 1; End: 20; Threshold: 37717.87890625
Well(s): A7-A9,B7-B9,C7-C9,D7-D9,E7-E9,F7-F9,G7-G9,H7-H9
Document: 090305 (Absolute Quantification)

Selected Detector: PTp6(2); Start: 3; End: 18; Threshold: 1164.43603516
Well(s): A10-A12,B10-B12,C10-C12,D10-D12,E10-E12,F10-F11,G10-G11,H10-H12
Document: 090305 (Absolute Quantification)

Figure 15

Amplification of HPV16. The diffuse band is unincorporated primer. The sharp band higher up is HPV amplicon, 323 bp. Lane 1: $8\times10^6$ GU, Lane 2: $8\times10^5$ GU, Lane 3: $8\times10^3$ GU, Lane 4: $8\times10^2$ GU, Lane 5: negative control.

Figure 16

Amplification of HPV18. The diffuse band is unincorporated primer. The sharp band higher up is HPV amplicon, 323 bp. Lane 1: $8\times10^6$ GU, Lane 2: $8\times10^5$ GU, Lane 3: $8\times10^3$ GU, Lane 4: $8\times10^2$ GU, Lane 5: negative control.

Figure 17

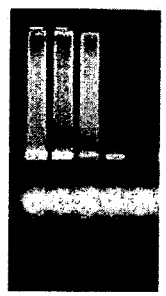

Amplification of HPV33. The diffuse band is unincorporated primer. The sharp band higher up is HPV amplicon, 323 bp. Lane 1: $8\times10^3$ GU, Lane 2: $8\times10^2$ GU, Lane 3: 80 GU, Lane 4: 8 GU, Lane 5: negative control.

Figure 18

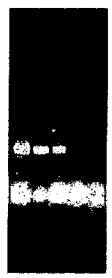

Amplification of HPV31. The diffuse band is unincorporated primer. The sharp band higher up is HPV amplicon, 323 bp. Lane 1: $8\times10^3$ GU, Lane 2: $8\times10^2$ GU, Lane 3: 80 GU, Lane 4: 8 GU, Lane 5: negative control.

Figure 19

Amplification of HPV56. The diffuse band is unincorporated primer. The sharp band higher up is HPV amplicon, 323 bp. Lane 1: $8 \times 10^4$ GU, Lane 2: $8 \times 10^3$ GU, Lane 3: $8 \times 10^2$ GU, Lane 4: 80 GU, Lane 5: negative control.

Figure 20

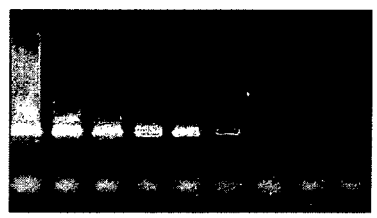

Amplification of HPV35. The diffuse band is unincorporated primer. The sharp band higher up is HPV amplicon, 323 bp. Lane 1: $8 \times 10^7$ GU, Lane 2: $8 \times 10^6$ GU, Lane 3: $8 \times 10^5$ GU, Lane 4: $8 \times 10^4$ GU, Lane 5: $8 \times 10^3$ GU, Lane 6: $8 \times 10^2$ GU, Lane 7: 80 GU, Lane 8: 8 GU, Lane 9: negative control.

US 8,895,247 B2

METHOD FOR DETECTION OF HUMAN PAPILLOMAVIRUS (HPV) TYPE

FIELD OF THE INVENTION

The present invention relates to detection, typing and quantitation of human papillomaviruses (HPV) in clinical samples. More specifically, it relates to oligonucleotide sequences which can be used in amplification reactions and used for the simultaneously detection, typing and quantification of a plurality of HPV genomes and a diagnostic kit thereof.

BACKGROUND OF THE INVENTION

Human papillomavirus (HPV) infection was reported as a cause of cervical cancer in the 1980's. The relationship between cancer malignancy and HPV genotype was considered to be of interest. More than 120 HPV types have since then been identified. Thirteen of the HPV types are recognised as being oncogenic in mucosal epithelia. These types include HPV 16, 18, 31, 33, 35, 39, 45, 51, 52, 56, 58, 59 and 66.

Human papillomavirus infections are confined to the epithelium, which limits their contact with the immune apparatus and they are poorly immunogenic. Thus serology is not a useful test for HPV. Similarly, culture is not a useful diagnostic technique. Although it is possible to reproduce the virus life cycle in vitro, this is a highly sophisticated tissue culture technique requiring in vitro differentiating epithelial cell cultures. Furthermore, high grade cervical neoplasias and cancers do not produce virus. Therefore, HPV testing relies on the detection of viral nucleic acids.

HPV testing has been shown to have a higher sensitivity than the PAP test (Papanicolaou test) for high-grade cervical dysplasia, although its specificity is lower due to the high prevalence of benign, transient HPV infections.

Many countries have adopted HPV testing as a secondary screening (triage) test for low-grade and equivocal dysplasia and its use as in primary screening has also been suggested.

The dominant HPV test is at present the Digene HCII test, whose utility is supported by a large body of scientific literature. In this test HPV DNA in the sample is hybridised to complementary RNA and the resulting DNA-RNA hybrids are captured by antibodies on a solid surface where they subsequently bind antibody-enzyme conjugates that are detected by enzyme-catalysed chemiluminescence. The LCII test does not distinguish between the different oncogenic HPV types.

It is also possible to detect HPV in fixed cells using in-situ hybridisation with probes labelled either with fluorescent moieties (fluorescence in-situ hybridisation, FISH) or with haptens that can bind to an enzyme conjugate which generates an insoluble coloured precipitate in situ. In situ hybridisation can provide valuable information on the location and physical state of HPV, but type specific detection of multiples of HPV types in the same sample is impracticable.

Many screening authorities express a preference for genotyping tests in secondary screening since this allows serial transient infections which are benign, to be distinguished from type-specific persistent infections which are not benign. In addition, some HPV types, particularly HPV16, are markedly more oncovirulent.

Finally, the use of a genotyping test provides useful epidemiological information which will be of particular value in monitoring the population effects of vaccination against HPV16 and HPV18.

The available HPV genotyping tests are mostly based on PCR followed by reverse hybridisation in some format. The PCR step targets the L1 or the E1 genes. PCR amplicons are labelled under amplification and hybridised to immobilised probes on a microarray, a membrane strip or in the wells of a microtiter plate. The bound labelled amplicon is then detected, either directly by fluorimetry if the amplicon is labelled with a fluorescent moiety or using enzyme conjugates that bind to the label and which are detected using colorimetric or luminometric techniques. Such tests involve handling of PCR amplicons in the open laboratory which necessitates stringent hygienic precautions. This, combined with the high price of such tests places the available tests beyond the reach of most mass-screening programs.

A genotyping test that detects mRNA from the viral oncogenes E6 and E7 using SDA (sequence dependent amplification) is also available. However, this method detects only five of the thirteen oncogenic types and only when there is active oncogene expression.

WO 2007115582 A1 describes sets of PCR primers and probes for detection of multiple HPV types by real-time PCR. These sets involves a complex combination of primers. In the method according to present invention, only one forward primer and four reverse primers are required. This simplifies quality control and manufacture and reduces cost. Further, the genes that are targeted in WO 2007115582 A1 are subject to intratypic sequence variation. This variation is not taken into account. Thus false negative results may occur in clinical samples that contain HPV sequence variants other than the prototype sequences. According to the present invention known sequence variation within the target region of the L1 gene has been taken into account prior to primer and probe design and all variant positions are either avoided or accounted for by modification of primer sequences.

Further, in WO 2007115582 A1 it is stated that sensitivities down to 100 copies for all targeted HPV types are achieved. However, the experiments described do not include the use of carrier DNA. This gives an unrealistically optimistic estimate of sensitivity as the human DNA present in clinical samples suppresses PCR sensitivity. The sensitivity of the method according to the present invention is measured in the presence of 500 ng of human DNA, which correspond to $7.5 \times 10^4$ human cells and thus accurately mimics the conditions in a cell-rich clinical sample. Thus the present invention provides enhanced sensitivity under realistic conditions.

Further, WO 2007115582 A1 describes the use of a single tube 13-plex multiplex PCR test. However, according to the state of the art there does not seem to be an instrument capable of performing such a test. The method according to the present invention may be operated on existing obtainable instruments in the format proposed or a variant or an analog thereof.

In WO 2009011472 A1 the target gene which has been used for the PCR tests is E1. However, this gene is a hotspot for deletions and insertions during cancer development. The probability of a false negative result increases thus with the severity of disease. The method according to the present invention targets the L1 gene, which is much less prone to deletion.

Further, in WO 2009011472 A1 the methods for detection and typing of HPV involve handling of PCR products in the open laboratory. This involves the risk of carry-over contamination. The method according to the present invention is performed in a closed-system which eliminates this risk, thus ensuring more reliable results and eliminating the extra labour required for decontamination of equipment and facilities after open-laboratory post-PCR work.

Based on the above, there is thus a need in the field for new methods, primers, probes and kits for detection and typing of HPV which are highly sensitive, reproducible and less expensive than the existing tests and which thus are appropriate for mass-screening programs.

SUMMARY OF THE INVENTION

The present invention describes the development of a quantitative realtime PCR method using consensus primers and multiplexed type-specific TaqMan probes that allows sensitive and specific detection and typing of the thirteen oncogenic HPV types HPV16, 18, 31, 33, 35, 39, 45, 51, 52, 56, 58, 59 and 66. Further, the method according to the present invention detects HPV types HPV6, 11, 26, 40, 42, 43, 44, 53, 54, 61, 68, 70, 72, 73, 82.

More specifically, the present invention relates to a method for detecting and/or typing and/or quantitation of the presence of a human papillomavirus (HPV) type in a biological sample, the test comprising the following steps:
(i) amplification of a nucleic acid fragment of HPV in the presence of a DNA polymerase, forward PCR primer with an oligonucleotide sequence of SEQ ID NO:1 or an analog thereof, reverse PCR primer with an oligonucleotide sequence selected from the group consisting of: SEQ ID NO:2, SEQ ID NO:3, SEQ ID NO:4, SEQ ID NO:5 or SEQ ID NO:6 or an analog thereof, a probe with a oligonucleotide sequence selected from the group consisting of: SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:25, SEQ ID NO:26, SEQ ID NO:27, SEQ ID NO:30, SEQ ID NO:31, SEQ ID NO:32, SEQ ID NO:34, SEQ ID NO:35, SEQ ID NO:37, SEQ ID NO:38, SEQ ID NO:39, SEQ ID NO:41, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:55, SEQ ID NO:56, SEQ ID NO:57, SEQ ID NO:58, SEQ ID NO:59, SEQ ID NO:61, SEQ ID NO:62, SEQ ID NO:63, SEQ ID NO:64, SEQ ID NO:65, SEQ ID NO:66, SEQ ID NO:68, SEQ ID NO:70, SEQ ID NO:71, SEQ ID NO:72, SEQ ID NO:73, SEQ ID NO:74, SEQ ID NO:75, SEQ ID NO:77, SEQ ID NO:78, SEQ ID NO:79 and SEQ ID NO:80 or an analog thereof, labelled with a fluorescent dye and a quencher molecule, and an internal control;
(ii) detection of a change of fluorescence and determining HPV type.

Further, the method according to the present invention refers to detecting and/or typing and/or quantitation simultaneously the presence of HPV 18, 52, 59, 39, 51, 56, 66, 16, 45, 58, 31, 33 and 35 in a biological sample, the method comprising the following four parallel reactions:
Reaction 1-a) amplification of the nucleic acid fragments of HPV 18, 52 and 59 in the presence of
(i) a nucleic acid polymerase
(ii) a forward PCR primer with an oligonucleotide sequence of SEQ ID NO: 1 or an analog thereof,
(iii) a reverse PCR primer with an oligonucleotide sequence of SEQ ID NO: 2 or an analog thereof,
(iv) a probe with an oligonucleotide sequence of SEQ ID NO: 7, 8 and 9 or an analog thereof, labelled with a fluorophore and a quencher molecule and
b) detection of a change of fluorescence the wavelength thereof determining the HPV type 18, 52 and 59;
Reaction 2-a) amplification of the nucleic acid fragments of HPV 39, 51, 56 and 66 in the presence of
(i) a nucleic acid polymerase
(ii) a forward PCR primer with an oligonucleotide sequence of SEQ ID NO: 1 or an analog thereof,
(iii) a reverse PCR primer with an oligonucleotide sequence of SEQ ID NO: 3 or an analog thereof,
(iv) a probe with an oligonucleotide sequence of SEQ ID NO: 10, 11, 12 and 13 or an analog thereof, labelled with a fluorophore and a quencher molecule and
b) detection of a change of fluorescence the wavelength thereof determining the HPV type 39, 51, 56 and 66;
Reaction 3-a) amplification of the nucleic acid fragments of HPV 16, 45 and 58 in the presence of
(i) a nucleic acid polymerase
(ii) a forward PCR primer with an oligonucleotide sequence of SEQ ID NO: 1 or an analog thereof,
(iii) a reverse PCR primer with an oligonucleotide sequence of SEQ ID
(iv) a probe with an oligonucleotide sequence of SEQ ID NO: 14, 15 and 16 or an analog thereof, labelled with a fluorophore and a quencher molecule and
b) detection of a change of fluorescence the wavelength thereof determining the HPV type 16, 45 and 58;
Reaction 4-a) amplification of the nucleic acid fragments of HPV 31, 33, 35 and internal control in the presence of
(i) a nucleic acid polymerase
(ii) a forward PCR primer with an oligonucleotide sequence of SEQ ID NO: 1 or an analog thereof,
(iii) a reverse PCR primer with an oligonucleotide sequence of SEQ ID NO: 5 or an analog thereof,
(iv) a probe with an oligonucleotide sequence of SEQ ID NO: 17, 18, 19 and 20 or an analog thereof, labelled with a fluorophore and a quencher molecule and
(v) internal control and
b) detection of a change of fluorescence the wavelength thereof determining the HPV type 31, 33, 35 and internal control.

The present invention also refers to a primer for HPV amplification selected from the group consisting of: SEQ ID NO: 1, SEQ ID NO:2, SEQ ID NO: 3, SEQ ID NO:4, SEQ ID NO: 5 and SEQ ID NO:6.

Further, the invention refers to a probe for HPV detection and/or typing and/or quantitation selected from the group consisting of: SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:25, SEQ ID NO:26, SEQ ID NO:27, SEQ ID NO:30, SEQ ID NO:31, SEQ ID NO:32, SEQ ID NO:34, SEQ ID NO:35, SEQ ID NO:37, SEQ ID NO:38, SEQ ID NO:39, SEQ ID NO:41, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:55, SEQ ID NO:56, SEQ ID NO:57, SEQ ID NO:58, SEQ ID NO:59, SEQ ID NO:61, SEQ ID NO:62, SEQ ID NO:63, SEQ ID NO:64, SEQ ID NO:65, SEQ ID NO:66, SEQ ID NO:68, SEQ ID NO:70, SEQ ID NO:71, SEQ ID NO:72, SEQ ID NO:73, SEQ ID NO:74, SEQ ID NO:75, SEQ ID NO:77, SEQ ID NO:78, SEQ ID NO:79 and SEQ ID NO:80 or an analog thereof.

The present invention also refers to a diagnostic kit for detection and/or typing and/or quantitation of HPV in a biological sample, comprising forward and reverse primers, probes for HPV11, 16, 18, 26, 31, 33, 35, 39, 40, 42, 43, 44, 45, 51, 52, 53, 54, 56, 59, 59, 61, 66, 68, 70, 72, 73 and 82, internal positive control and DNA polymerase.

BRIEF DESCRIPTION OF THE FIGURES AND THE TABLES

FIGS. 1-13: shows analysis of samples and amplification curves for consensus multiplex realtime PCR type for the specific detection of HPV types 16, 18, 31, 33, 35, 39, 45, 51, 52, 56, 58, 59 and 66 wherein:

FIG. 1: shows amplification of HPV18 in multiplex group 1.

Figure 2:
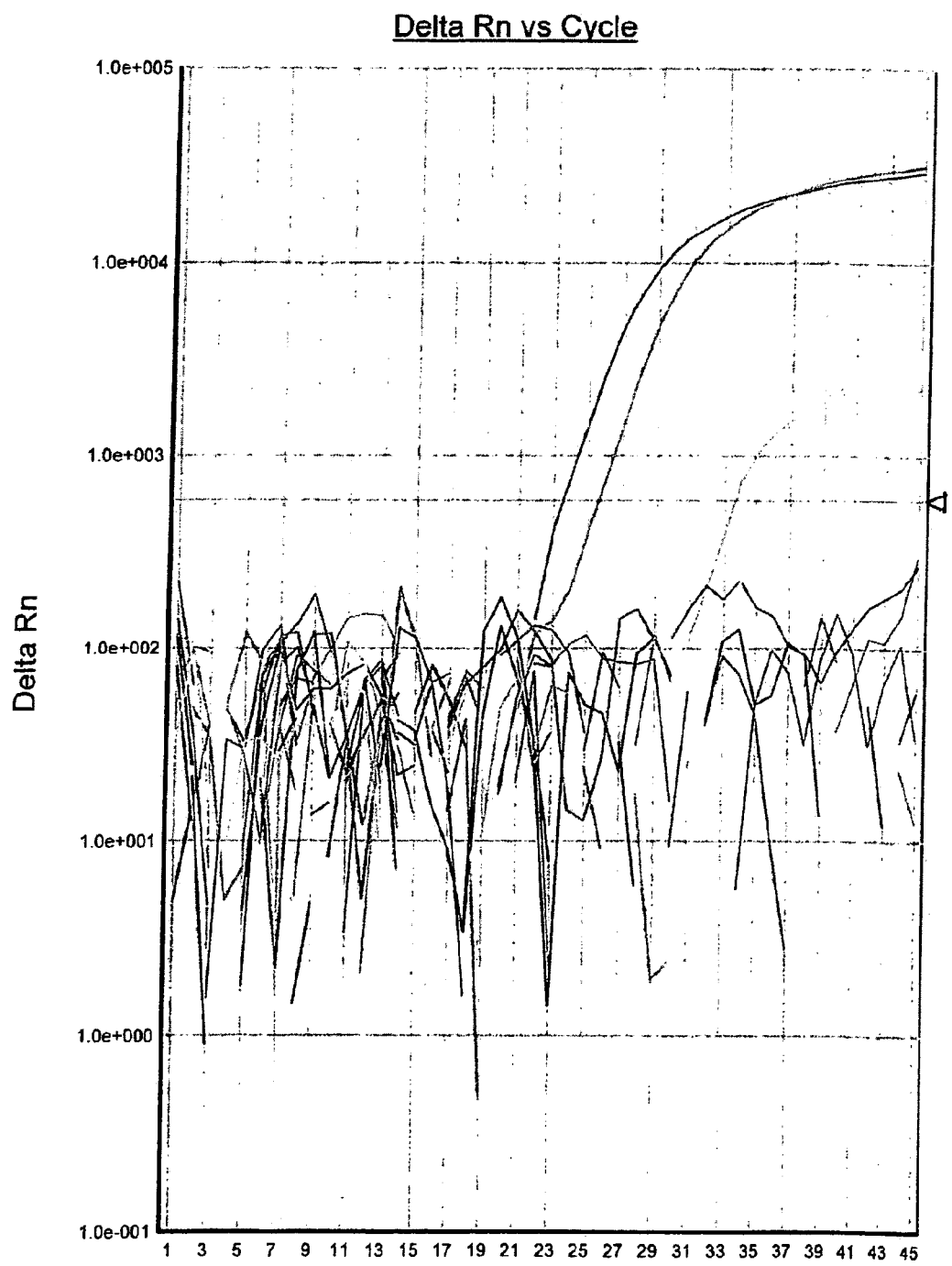

FIG. 2: shows amplification of HPV52 in multiplex group 1.

Figure 3:
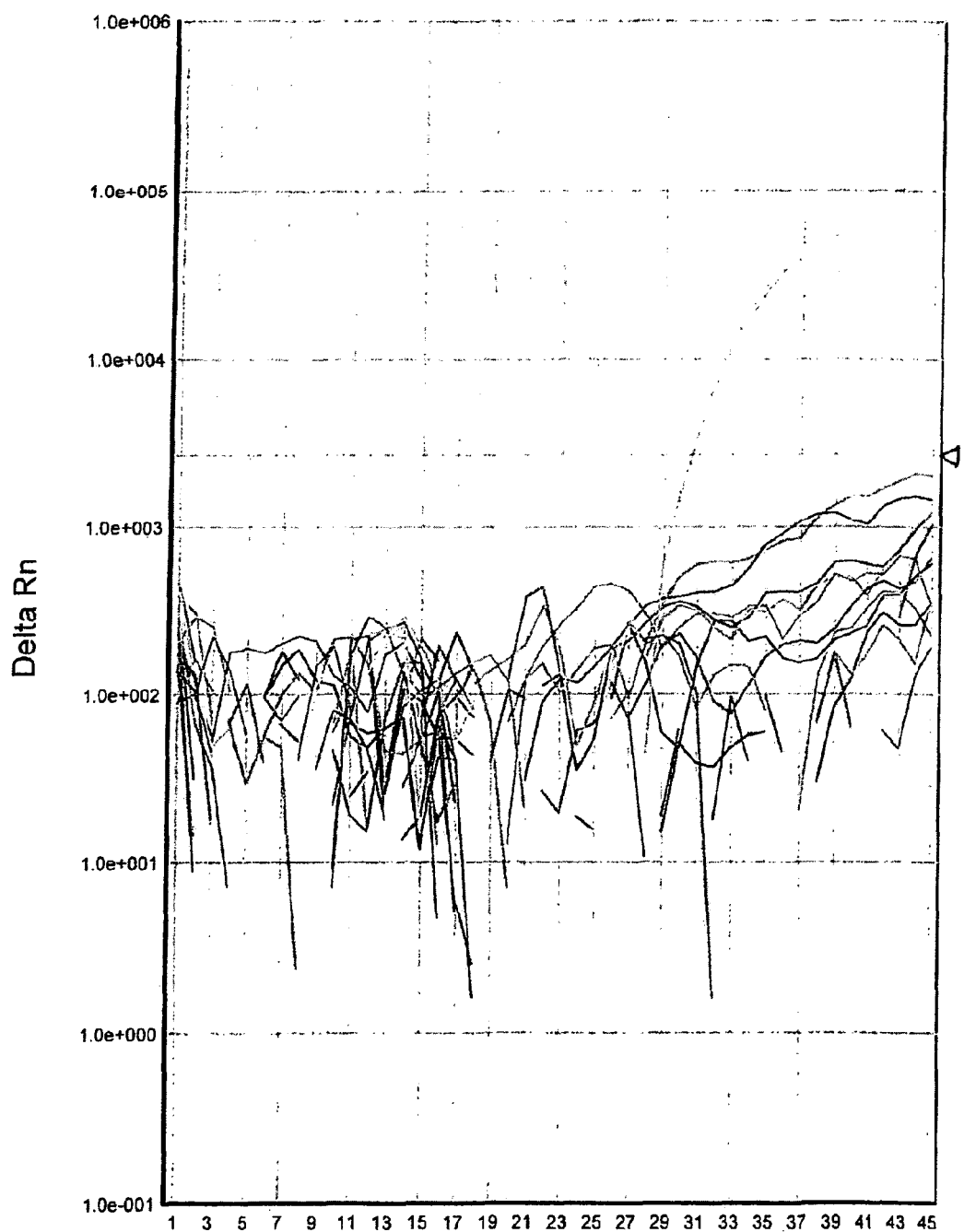

FIG. 3: shows amplification of HPV59 in multiplex group 1.

Figure 4:
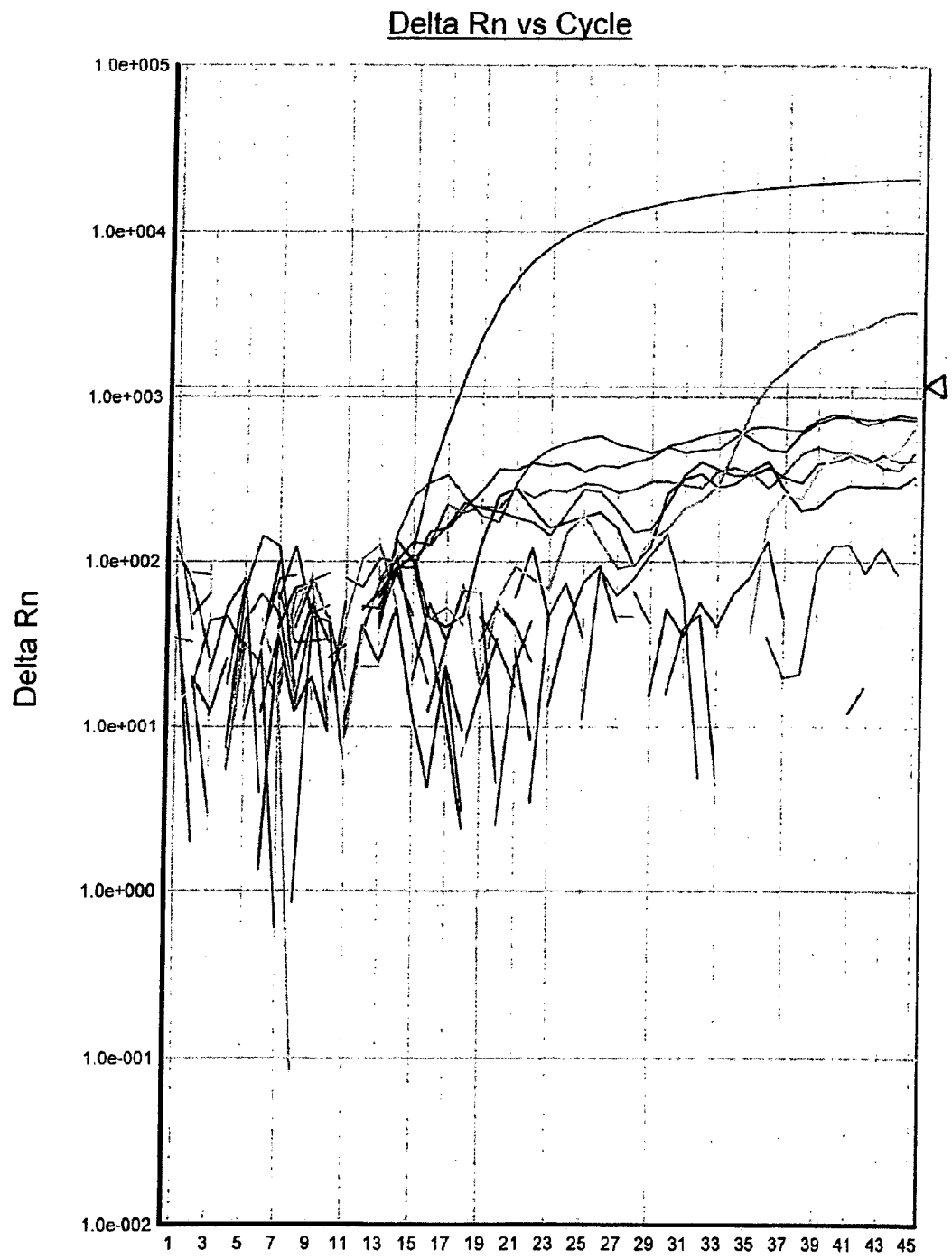

FIG. 4: shows amplification of HPV39 in multiplex group 2.

Figure 5:
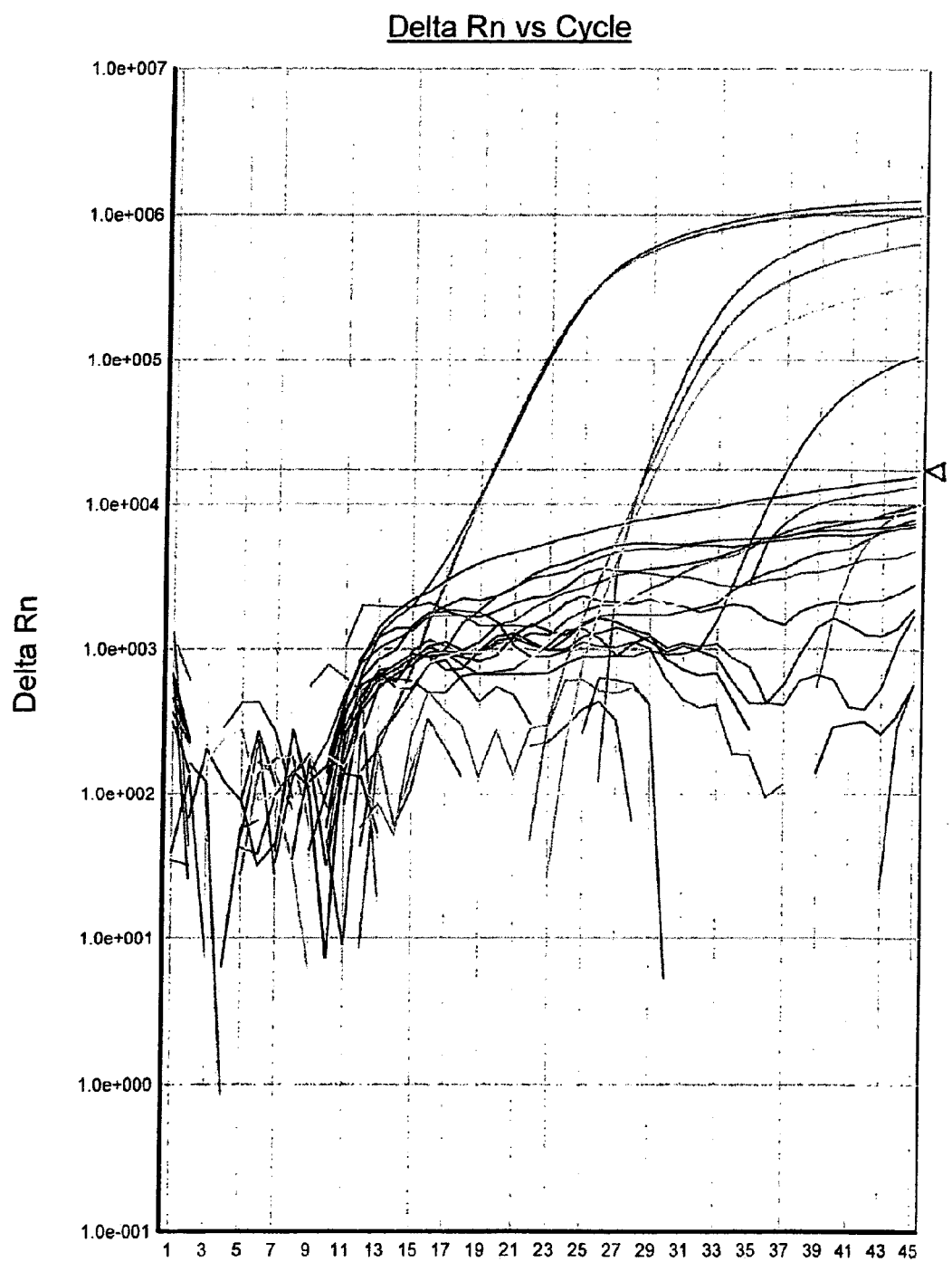

FIG. 5: shows amplification of HPV51 in multiplex group 2.

Figure 6:
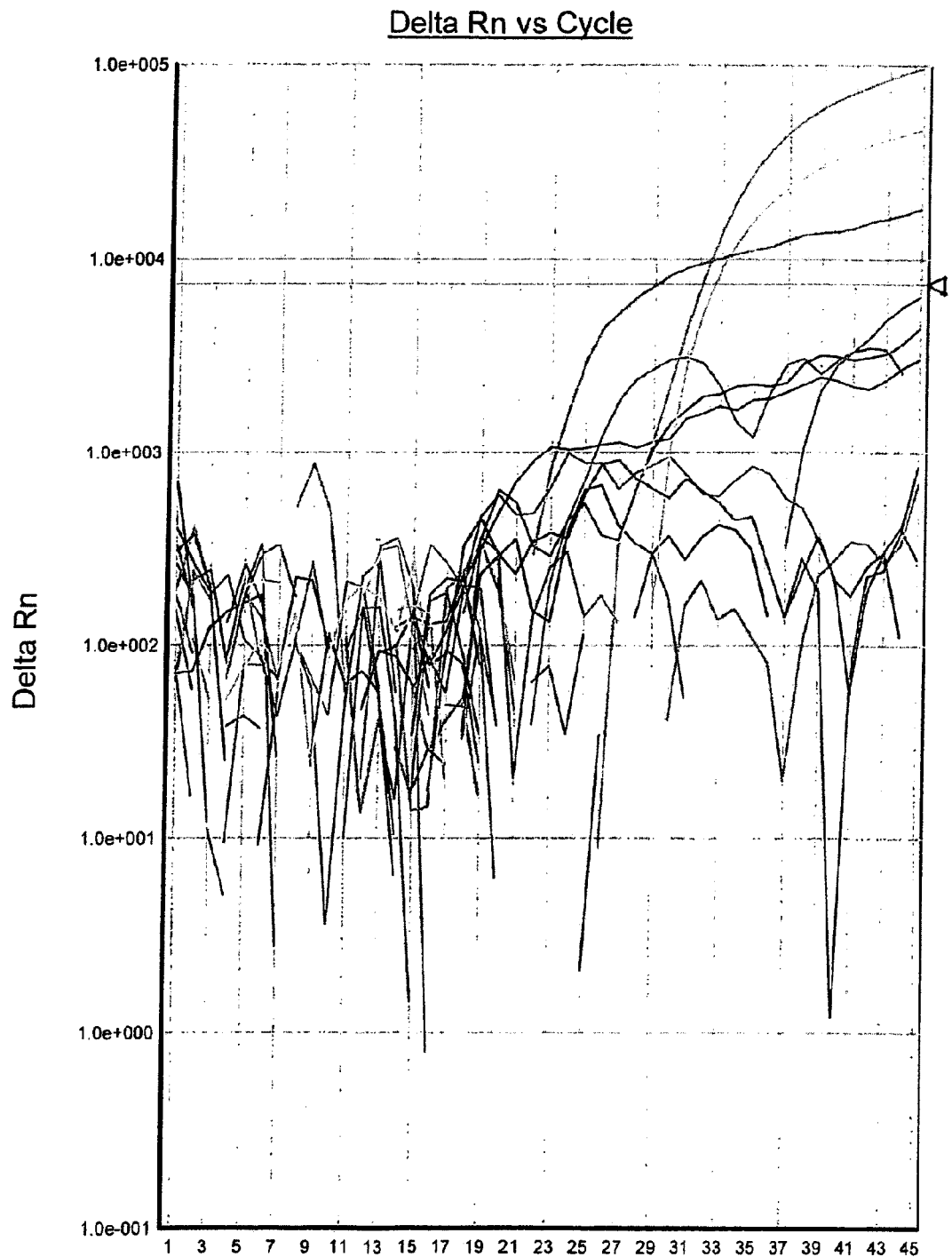

FIG. 6: shows amplification of HPV56 in multiplex group 2.

Figure 7:
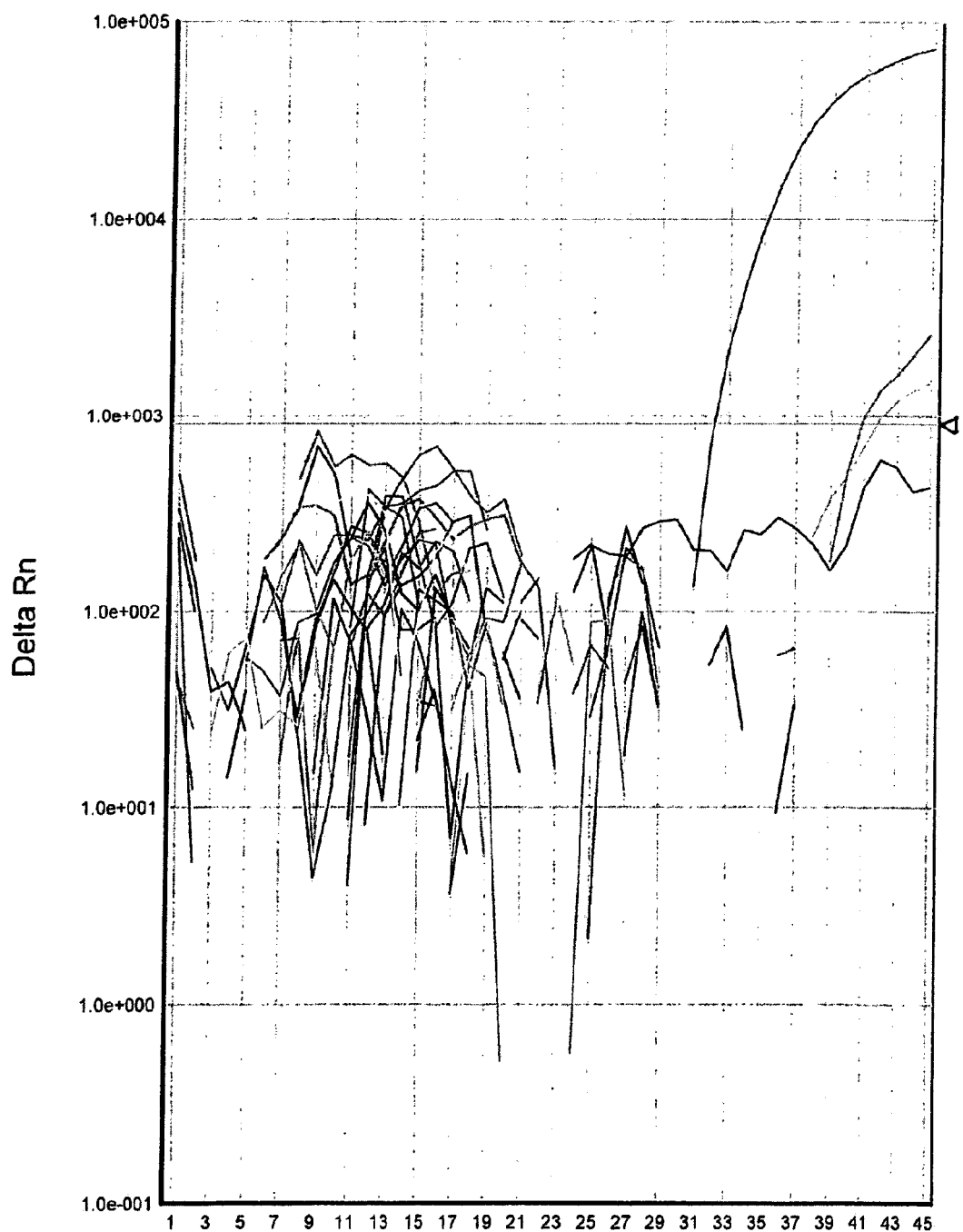

FIG. 7: shows amplification of HPV66 in multiplex group 2.

Figure 8:
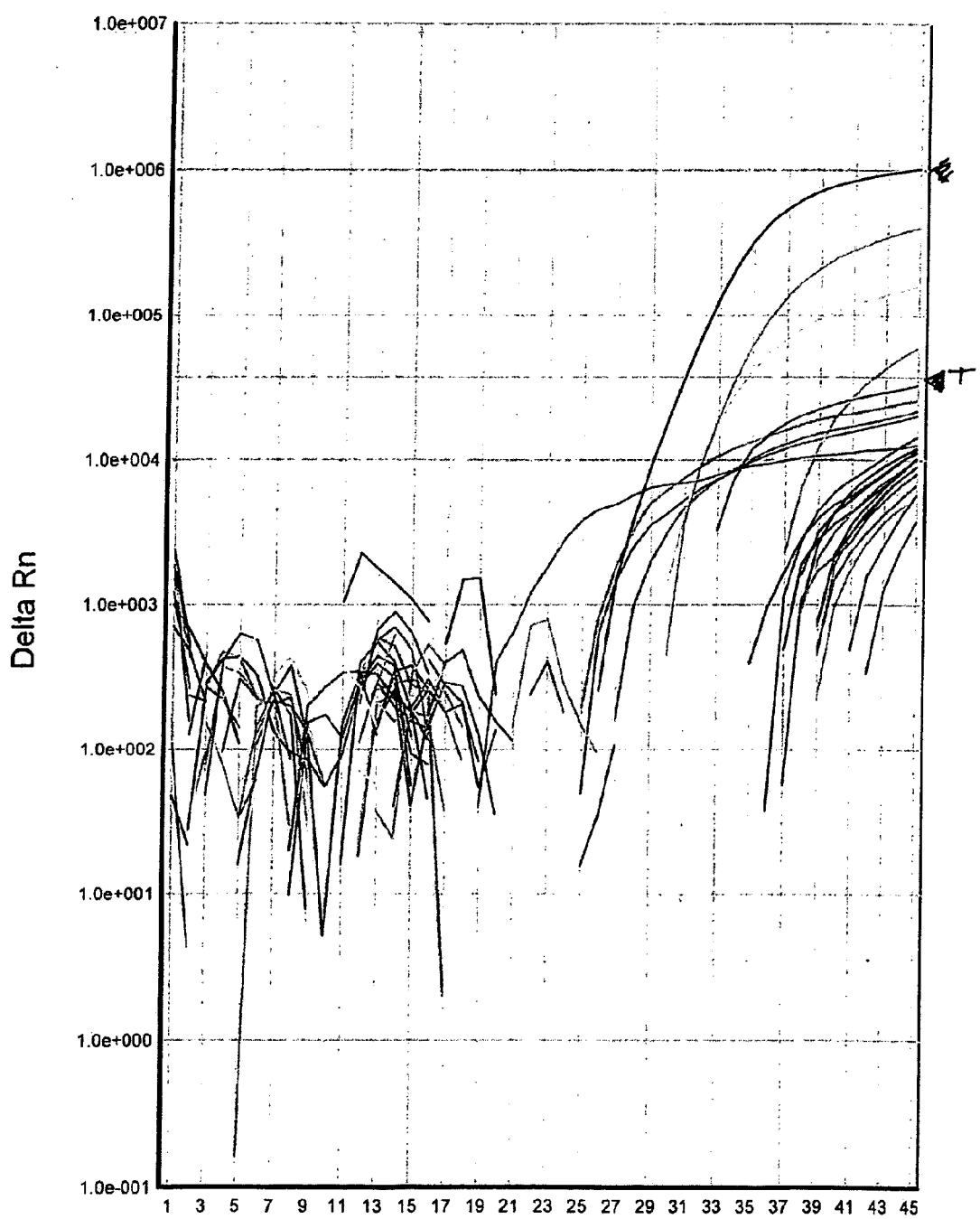

FIG. 8: shows amplification of HPV16 in multiplex group 3.

Figure 9:
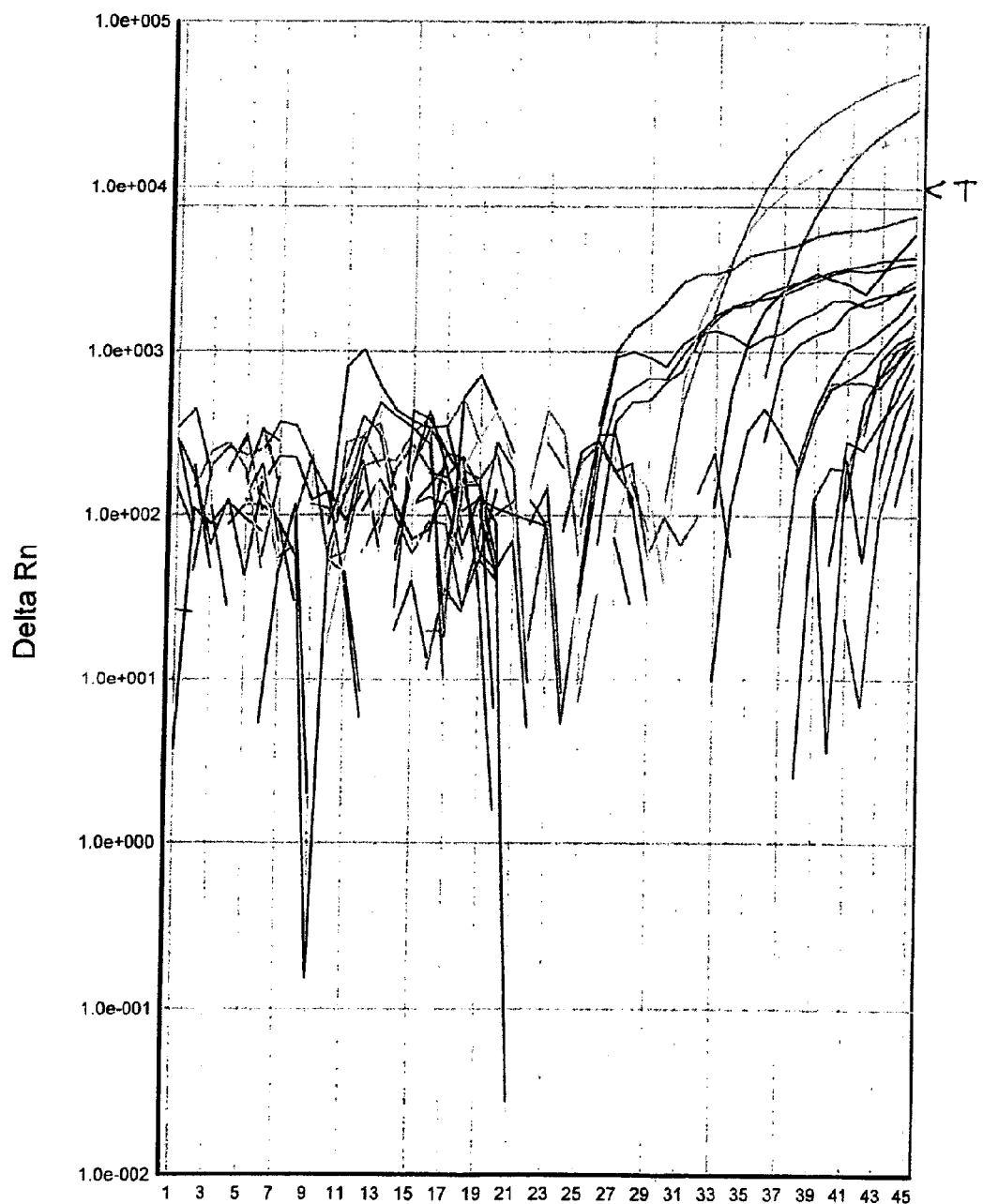

FIG. 9: shows amplification of HPV45 in multiplex group 3.

Figure 10:
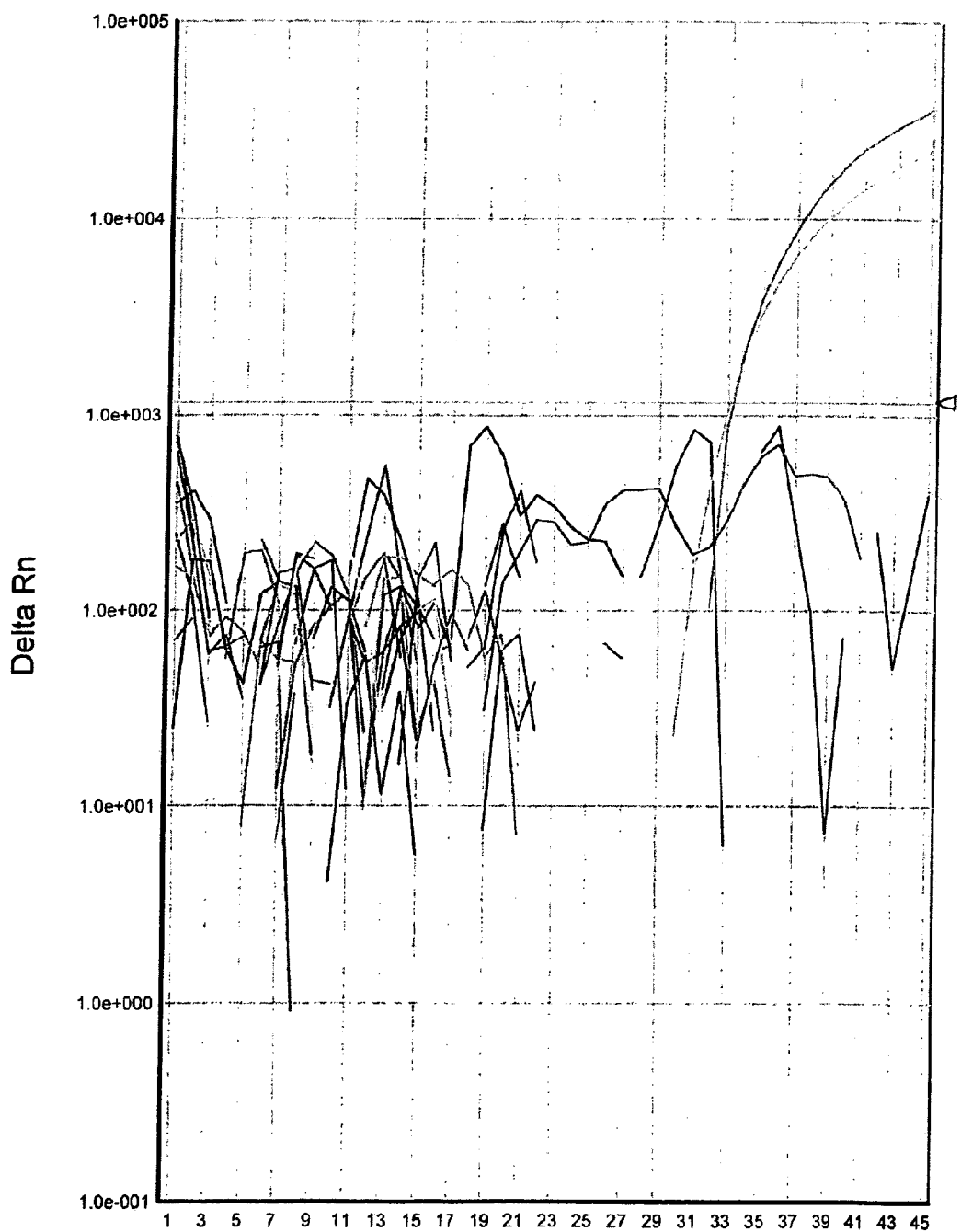

FIG. 10: shows amplification of HPV58 in multiplex group 3.

Figure 11:
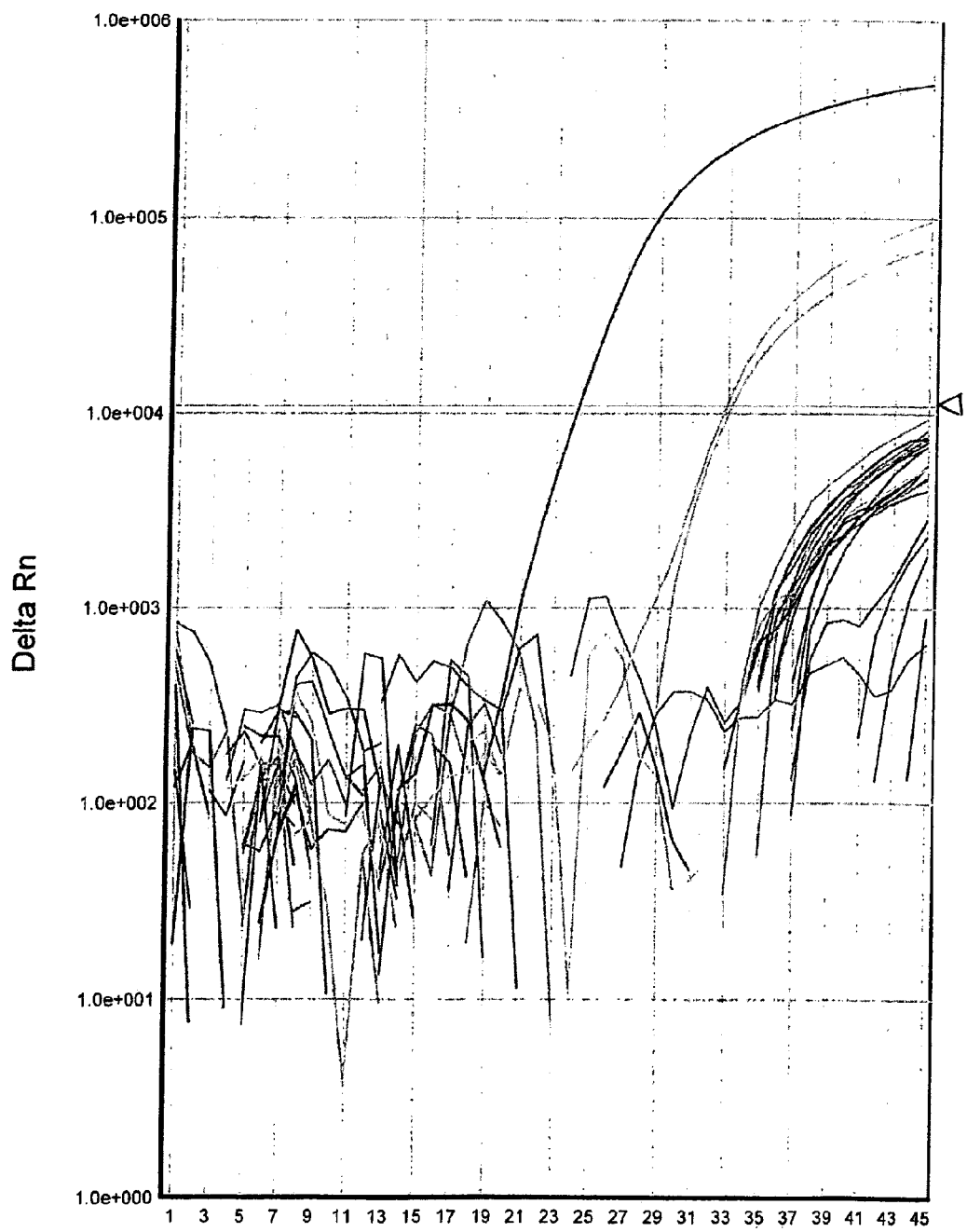

FIG. 11: shows amplification of HPV31 in multiplex group 4.

Figure 12:
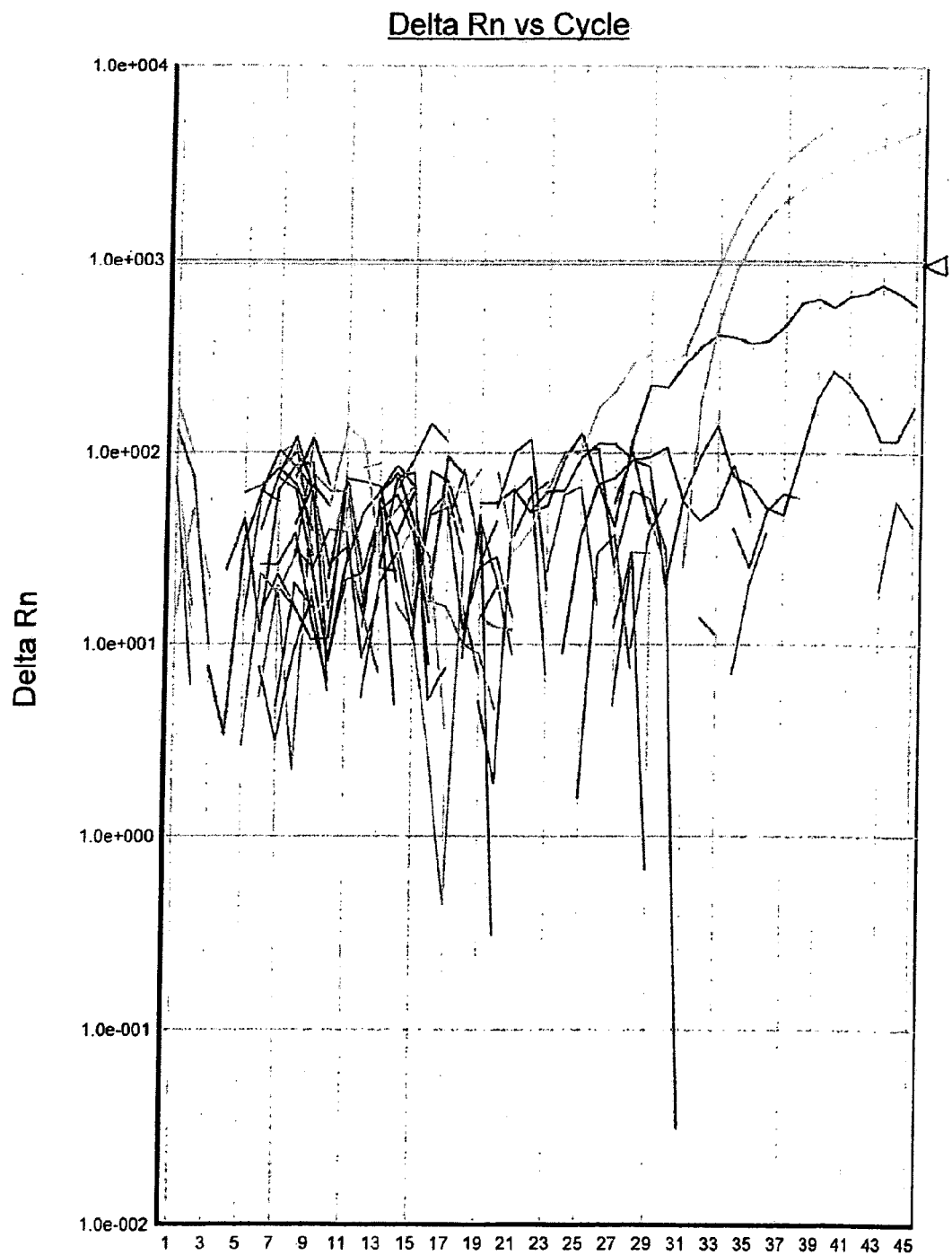
Figure 13:
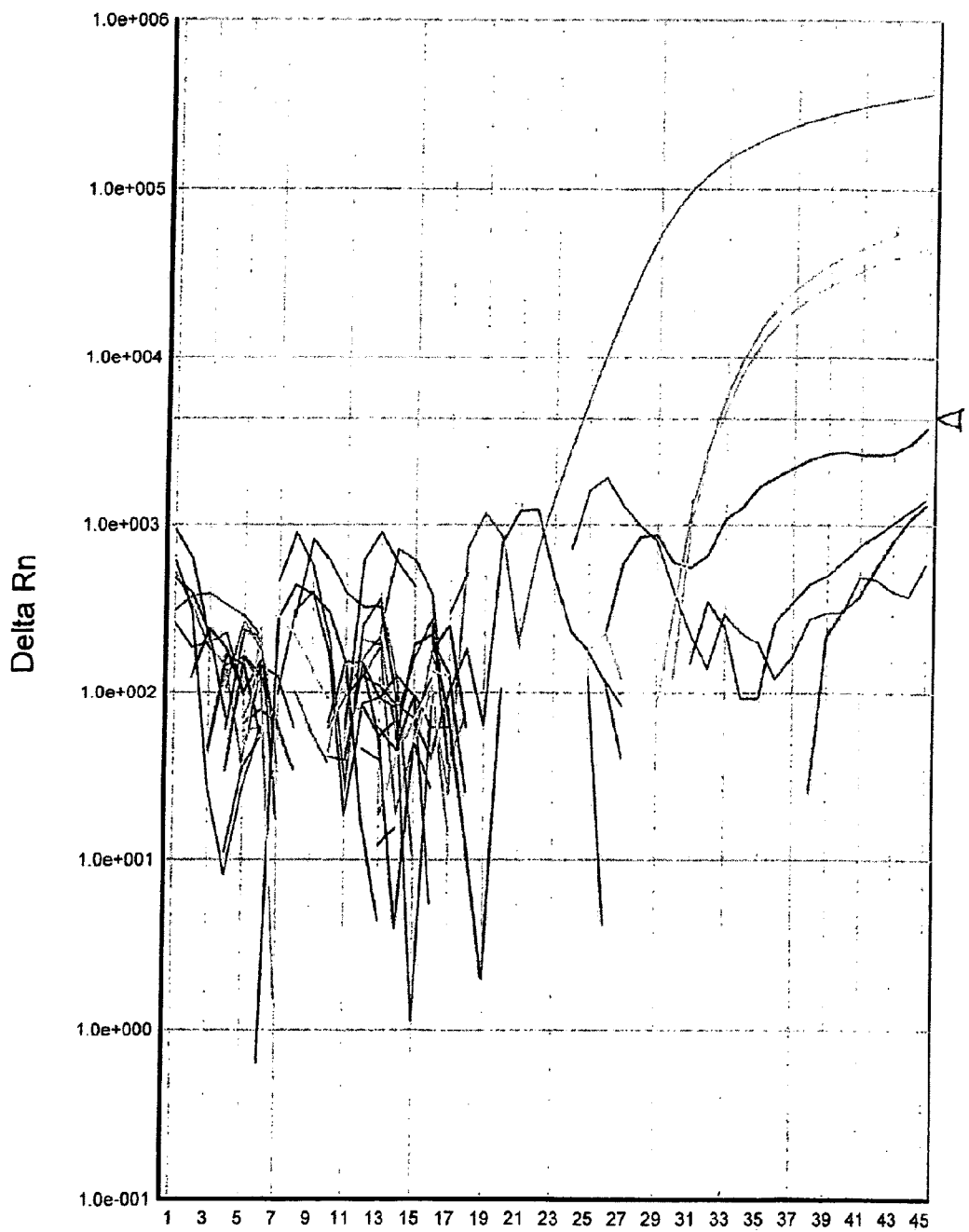

FIG. 12: shows amplification of HPV33 in multiplex group 4 FIG. 13: shows amplification of HPV35 in multiplex group 4.

Figure 14:
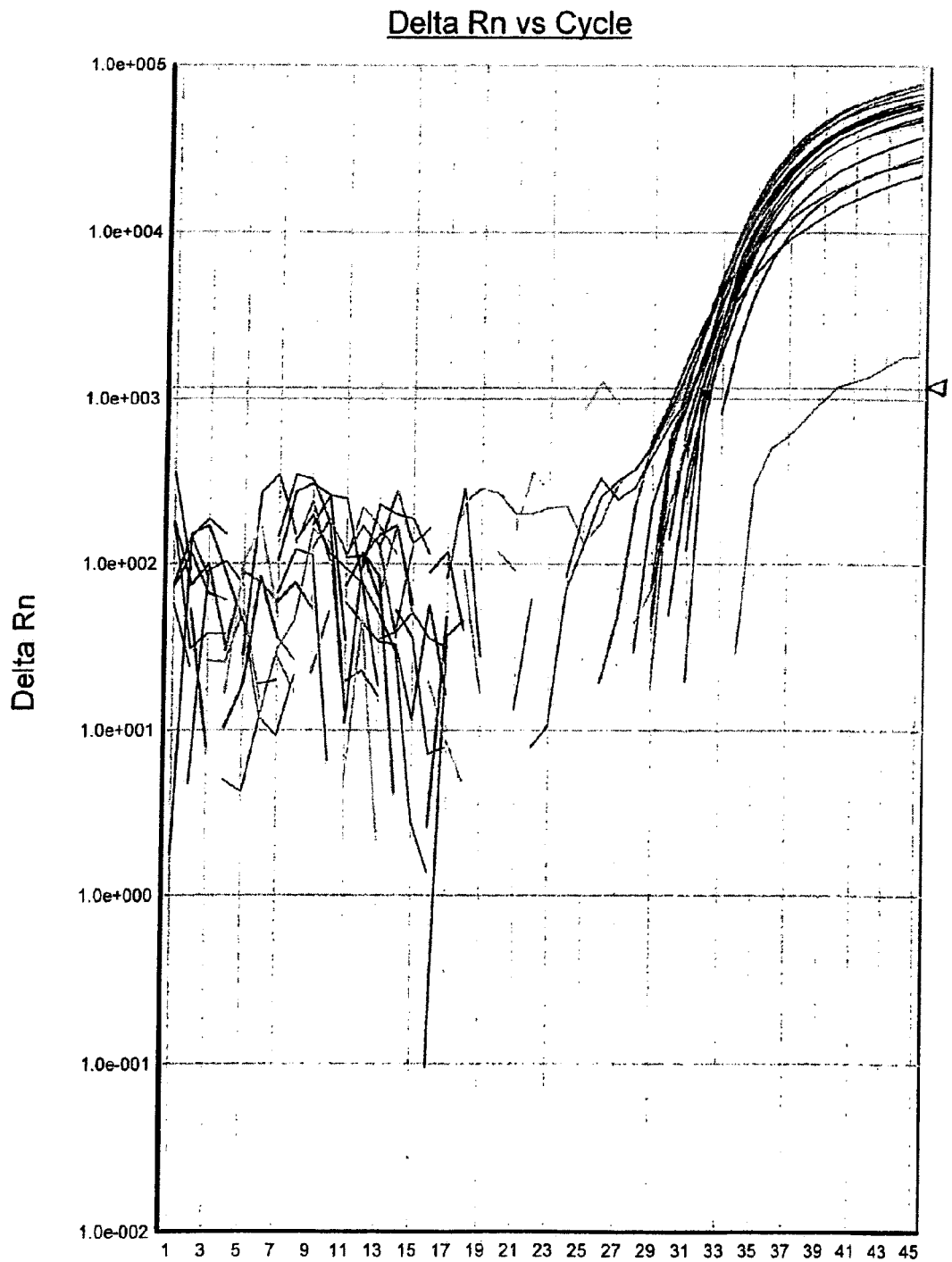

FIG. 14: shows amplification curves for the internal control.

FIGS. 15-20: show amplification of dilution series of HPV16, HPV18, HPV31, HPV33, HPV35 and HPV56 with primers PTf and PTr2.

Table 1: Refers to the list of designed primers.
Table 2: Refers to the list of designed probes.
Table 3: Refers to the composition of the Multiplex PCR of Multiplex Group 1, Multiplex Group 2, Multiplex Group 3 and Multiplex Group 4.
Table 4: Refers to evaluation of consensus realtime method on clinical samples.
Table 5: Refers to HPV Group 1, mastermix formulation.
Table 6: Refers to HPV Group 2, mastermix formulation.
Table 7: Refers to HPV Group 3, mastermix formulation.
Table 8: Refers to HPV Group 4, mastermix formulation
Table 9: Refers to the analytical sensitivity for the target HPV types.

DETAILED DESCRIPTION OF THE INVENTION

The quantitative realtime PCR method according to the present invention detects all the recognised oncogenic mucosal HPV types down to levels of 400 GU per sample or less. The method is intrinsically semi-quantitative since results are read off as $C_T$ values which are proportional to the initial concentration of target DNA. It is also possible to run the reactions in a fully-quantitative mode by including dilution series of the target type(s) in order to construct standard curves.

The quantitative nature of the method has several advantages. In epidemiological studies it would be possible to establish a constant cutoff value for all types, thus eliminating the biased prevalence estimates that result from type-specific differences in analytical sensitivity. It has been suggested that only high-level HPV infections of greater 50 000 GU per sample are clinically significant, although this remains a matter of debate. In the consensus multiplex method it is possible to adjust the cutoff to any quantitative value required. Lastly, use of a quantitative method may be of use in following the progress of infections and the effects of treatment.

The analytical sensitivity of the method is 4-400 GU for all types in the presence of 500 ng of human DNA, which corresponds to $0.75 \times 10^5$ cells. Thus the presence of a single virus copy in 0.5% of the cells would give a positive result. At lower human DNA concentrations (50 ng), corresponding to $0.75 \times 10^4$ cells, the sensitivity improves by a factor of 10. This means that false positive results due to cell-poor samples are unlikely to be a problem. However, it also implies that operating the test in a fully quantitative mode will require standardisation of the cellular DNA concentration.

Compared with the hybrid capture (HCII) test, HPV was detected in more clinical samples, as is expected considering that the detection sensitivity of the consensus multiplex method according to the present invention was at least an order of magnitude higher.

The method according to the present invention thus covers all confirmed oncogenic HPV types in one test. The method has been specifically designed to give a four-tube format. This gives a method that optimally uses the 8×12 (96-well) and 16×24 (384 well) formats that are standard in most realtime PCR instruments. However, it is obvious that the method according to the present invention may be used in a different format without departing from the scope of the invention.

Further, in the method according to present invention, only one forward primer and four reverse primers are required. This simplifies quality control and manufacture and reduces cost.

According to the present invention known sequence variation within the target region of the L1 gene has been taken into account prior to primer and probe design and all variant positions are either avoided or accounted for by modification of primer sequences.

The sensitivity of the method according to the present invention is measured in the presence of 500 ng of human DNA, which correspond to $7.5 \times 10^4$ human cells and thus accurately mimics the conditions in a cell-rich clinical sample. This provides for an enhanced sensitivity for all targeted HPV types.

The method according to the present invention targets the L1 gene, which is much less prone to deletion.

The primers according to the present invention could with further modifications be used for the detection of related HPV types such as inter alia HPV11, 26, 40, 42, 43, 44, 53, 54, 61, 68, 70, 72, 73, 82.

In the real-time PCR instrument used in the method according to the present invention there are two vacant colour channels which allows the possibility of adding further oncogenic HPV types to the test.

The multiplex grouping described in the present application is one of a number of possible groupings. For example the primers used in group 3 are known to be able to amplify HPV types 18, 31, 33, 39, 51, 58, 59 and 66 and the internal control HPV6, and thus any of these types might therefore be assigned to this group.

In the present invention a real-time PCR instrument is used having four colour channels. However with real-time PCR instruments having five, six, seven or more colour channels alternative variants of the test would be possible. The primers and probes could then be combined in three or two parallel reactions for detection of the same HPV types.

In the present test format 20 samples can be analysed in one working day, making the test most suitable for low- to moderate-throughput laboratories. Larger batches of samples could be analysed using a 384-well format realtime PCR instrument, although the capacity of available automatic DNA extraction instruments is at present a more important limit on throughput than the PCR analysis time.

Realtime PCR is a closed-system test. It is thus not necessary to handle amplified samples in the open laboratory. Problems of PCR carry-over contamination are thus greatly reduced, and this in turn reduces the resources that must otherwise be devoted to the stringent contamination control associated with open-laboratory post-PCR analysis.

The method according to the present invention is inter alia of value in screening programs where HPV genotyping is preferred.

Preferred embodiments of the invention are described. However it is to be understood that the invention is not limited to those precise embodiments, and that various changes and modifications may be effected therein by one skilled in the art without departing from the scope or spirit of the invention as defined in the appended claims. The following examples illustrate, but do not limit the invention.

EXAMPLES

Example 1

Plasmids

Plasmids containing the target region of the L1 genes of HPV6, 16, 18, 31, 33, 35, 39, 45, 51, 52, 56, 58, 59 and 66 were transformed into *Escherichia coli* DH5-alpha and isolated by caesium chloride density gradient centrifugation (Fritsch et al) or Qiagen HiSpeed Midi Kit (Qiagen GmbH, Hilden, Germany). DNA concentrations were determined by ultraviolet spectrophotometry.

Example 2

Clinical Samples

Clinical samples were cervical cytobrush samples sent to our laboratory for routine HPV analysis for secondary screening of low grade dysplasia (LSIL) or equivocal cytology (ASCUS or inadequate sample). Samples were collected and transported in CYTYC thin prep transport (medium CYTYC, Crawley, UK) according to the manufacturers recommendations. 10 ml of sample was centrifuged at 3000 rpm for 10 min and the pellet was resuspended in 100 µl phosphate buffered saline before extraction of DNA using the MagNAPure automatic DNA extraction instrument with the MagNAPure LC DNA extraction kit (Roche Diagnostics, Penzberg, Germany). DNA was eluted in 100 µl. Clinical specimens that had previously been tested with the HCII test and typed using a consensus PCR and reverse line blot were used to evaluate the test.

Example 3

Hybrid Capture Test

The Digene Hybrid Capture Test (Digene, Gaithersburg, Md.) was performed using 25 ml of sample according to the manufacturers' instructions.

Example 4

Primer Design

In order to identify suitable targets for consensus PCR primers, the sequences of the L1 genes of HPV types 16, 18, 31, 33, 35, 39, 45, 51, 52, 56, 58, 59 and 66, plus HPV6 were aligned using CLUSTALW. In order to generate input sequences for the CLUSTAL alignments the prototype sequence of each HPV type was used in a BLAST search in order to identify intratypic variant sequences. The sequence was then edited at variant position by the substitution of the appropriate IUPAC ambiguity code. The regions corresponding to nt 6348-6374 and 6579-6557 on the HPV16 genome were identified as highly conserved and were chosen for the placing of the forward and reverse primers respectively. This led to the construction of Primers PTf and PTr. As this primer pair did not amplify all target types satisfactorily, a phenomenon which could be attributed to low stability of duplexes with PTr, less degenerate version of PTr were sought.

The sequences were grouped into four homology groups on the basis of a distance tree of the concatenated forward and reverse primer target sequences constructed in CLUSTALW (http://www.ebi.ac.uk/Tools/clustalw2/index.html). The groups were HPV18, HPV52 and HPV59 (Group 1), HPV39, HPV51, HPV56 and HPV66 (Group 2), HPV16, HPV45 and HPV58 (Group 3) and HPV31, HPV33 and HPV35 plus the internal control HPV6 (Group 4). For each group a new CLUSTAL alignment was constructed and group-specific reverse primers were designed in order to reduce primer degeneracy and improve sensitivity. Variable positions were accommodated by using inosine as a wildcard base, thymine as a universal pyrimidine, guanine as a universal purine (exploiting the stability of the noncanonical G:T basepair) or incorporating mixed nucleotides. This led to the design of primers PTrGr1, PTrGr2 and PTrGr4. The original PTr sequence was retained for group 3.

An alternative target region corresponding to positions 6644-6620 on HPV16 was also investigated for placing of the reverse primer. The primer PTr2, was designed to target this region. PTr2 is suitable for the amplification of HPV types 16, 18, 31, 33, 35, 45, 52, 56, 58, 58 and 59.

TABELL 1

List of primers

| Primer | Sequence | SEQ ID NO |
|---|---|---|
| PTf | 5-TG(CT)AAA TAT CC(AT) GAT TAT (AT)TI IAA ATG-3 | 1 |
| PTrGr1b | 5-TGT AGC CAG TAT GG(CT) TTA TTG AA-3 | 2 |
| PTrGr2 | 5-TG(GT) AGC CAA TAA GGT TTA TTA AA-3 | 3 |

TABELL 1-continued

List of primers

| Primer | Sequence | SEQ ID NO |
|---|---|---|
| PTr957 | 5- TGI AIC CAA TAI GG(CT) TTA TTG AA -3 | 4 |
| PTrGr4 | 5- TGT AIC CAA TAT GGt TTA TTA AA-3 | 5 |
| PTr2 | 5- C(GT)G T(AG)G TAT CIC CAI CAA GTA ACA AA-3 | 6 |

Example 5

Probe Design

TaqMan MGB probes were designed using Primer Express software (Applied Biosystems, Foster City, Calif.) using the target amplicon as input sequence and specifying an amplicon length of 200 bp. The software was set to find primers with a Tm of 60° C. and probes with a Tm 10° C. higher (70° C.). Where necessary, in order to compensate for the software's inability to locate probes without simultaneously locating primers, the sequence was bracketed by dummy primer sequences. TaqMan MGB probes were supplied by Applied Biosystems and were labelled with FAM, VIC or NED which are the recommended labels for the three standard colour channels of the AB Prism 7000 series of realtime PCR instruments. MGB probes incorporate a minor groove binder, which raises probe Tm and allows shorter probes to be used, and a dark (non-fluorescent quencher). A fourth channel, usually used for a passive reference, is available on ABI 7000 series instruments. This channel ideally uses the dye ROX. ROX-labelled MGB probes are not obtainable. In order to achieve the required Tm, two approaches were employed. In the first approach probes were first designed as TaqMan MGB probes, then redesigned as LNA probes on the basis of the suggestions of the suppliers (Sigma Genosys,) or using the website http://lna-tm.com/. LNA probes incorporate a modified deoxyribose in the sugar-phosphate backbone that stabilises the helical structure and increases Tm. Alternatively Primer Express was used to design conventional (non-MGB) TaqMan probes using the program module for this purpose and probes <22 by were further evaluated. All probes were designed with a Tm of 70±2° C. ROX-labelled probes were fluorophor-labelled at the 5' end and quenched with the dark quencher BHQ2 at the 3' end. Candidate probes were compared with CLUSTALW multiple sequence alignments of the amplicon region of the thirteen target HPV types and HPV6 with variant positions marked. Probe sequences targetting intra-type invariant but inter-type specific sequences were selected for further testing.

Example 6

PCR Program

All PCR reactions were run on the ABI Prism 7000 or 7300 genetic analyzer (Applied Biosystems, Foster City, Calif.) with the ROX passive reference function disabled in order to allow the ROX colour channel to be used for detection. For all experiments the PCR program was: 95° C., 12 min followed by 45 cycles of 95° C., 15 s; 45° C., 30 s; 60° C., 60 s. For experiments using SYBR green, dissociation analysis was appended to the end of the program. The reaction volume was 50 µl and 5 µl of sample DNA was used in all reactions. PCR mastermixes were used according to the manufacturers instructions.

Example 7

Testing of Primers

Primers were used at a concentration of 600 nM. Analytical sensitivity was assessed for all target HPV types by amplifying 10-fold dilution series of HPV plasmid DNA in 100 ng/µl human DNA (Sigma Aldrich, St Louis, Mich.). Amplified DNA was detected using SYBR green with the Finnzymes DyNAmo SYBR green qPCR kit F400 (Finnzymes, Espoo, Finland) using the PCR program described combined with dissociation analysis. Analytical sensitivity was defined as the lowest target concentration that gave an unequivocal type-specific dissociation peak. The criterion for primer acceptability at this stage of the analysis was an analytical sensitivity of 4000 GU or better for all target HPV types.

Example 8

Probe Assessment and Titration

Probes were initially used at a concentration of 200 nM. Assessment of probes was done by TaqMan PCR assay using Finnzymes DyNAmo probe PCR kit F450 (Finnzymes, Espoo, Finland) or, in later experiments, PerfeCta qPCR FastMix, UNG Quanta Mastermix (Quanta Biosciences, Gaithersburg, Md.) using a 10-fold serial dilution of the target HPV type in 100 ng/µl human DNA and the cognate primers. A positive amplification signal from 400 GU of target DNA was the minimum criterion for approval of the probe for further testing.

When used at high concentrations in multiplex reactions, probes tend to interfere with one another. Therefore probe titration was performed in order to determine the minimum probe concentration that could be used without loss of sensitivity. Probe concentrations of 200, 150, 100 and 50 nM were tested against 4000, 400, 40 and 4 GU of the target type. The lowest concentration of probe that could be used without loss of analytical sensitivity was used in multiplex reactions.

Example 9

Testing of Probes in Multiplex

For multiplex testing, the probes were combined at the chosen concentration together with the cognate primers and tested against dilution series of the three or four target HPV types in PCR reactions as described. Criteria for acceptance of a multiplex combination were analytical sensitivity 400 GU or better and no cross-reaction with the other types in the group. Where unacceptable loss of analytical sensitivity or cross-reaction were detected in a multiplex group, reactions were repeated with fewer probes in all combinations in order to identify the interfering probe.

Successful groups of probes were tested against $4.10^4$ GU of each of the fourteen HPV types in the test in order to detect cross-reaction. Where cross-reaction was observed, the cross-reacting probe was tested against the cross-reacting HPV type(s) in a simplex reaction in order to determine whether the cross-reaction was due to a direct interaction between the probe and the cross-reacting HPV type, or due to secondary effects caused by multiplexing.

Where probes were rejected due to interference or cross-reaction, new probes were designed and tested as described above.

The probes which were assessed are shown in table 2.

TABLE 2

List of probes

| GrpHPV | Sequence | SEQ ID NO | Label | Type | Target |
|---|---|---|---|---|---|
| 1 PTp18(7) | ATA CAC ACA GCT GCC AGG T | 21 | FAM | TaqMan MGB | HPV18 |
| 1 PTp18(8) | CTTCACCTGGCAGCTG | 22 | FAM | TaqMan MGB | HPV18 |
| 1 PTp18(130) | CACTGTGCCTCAATC | 23 | FAM | TaqMan MGB | HPV18 |
| 1 PTp18(131) | ACTGTGCCTCAATCC | 7 | FAM | TaqMan MGB | HPV18 |
| 1 PTp18(177) | ACCTGGCAGCTGTGT | 25 | FAM | TaqMan MGB | HPV18 |
| 1 PTp 52 | TCT AAC TCT GGC AAT A | 26 | ROX/BHQ2 | TaqMan MGB | HPV52 |
| 1 PTp52(4) | tc+Taa+Ctc+Tggc+Aa+Tac+Tgc | 8 | ROX/BHQ2 | LNA | HPV52 |
| 1 PTp 59(1) | TAC TGA CAT ACG TGC C | 9 | NED | TaqMan MGB | HPV59 |
| 1 PTp59(77q) | AGGCGAGAACAGGTTTTGCCAGACA | 29 | NED | TaqMan MGB | HPV59 |
| 1 PTp59(132) | ATCAACTTCCTGAATCACT | 30 | NED | TaqMan MGB | HPV59 |
| 1 PTp59(159) | AAGGTACTGACATACGTGCC | 31 | NED | TaqMan MGB | HPV59 |
| 2 PTp 39(1) | CAC AGA TAT ACG TGC AAA | 32 | ROX/BHQ2 | TaqMan MGB | HPV39 |
| 2 PTp39(4) | ca+Ca+Gatat+Acg+Tg+Caa+Acc | 10 | ROX/BHQ2 | LNA | HPV39 |
| 2 PTp39(5) | caca+Gatat+Acg+Tg+Caa+Acc | 34 | ROX/BHQ2 | LNA | HPV39 |
| 2 PTp 51 | AGT GGT AAT GGC CGT G | 35 | FAM | TaqMan MGB | HPV51 |
| 2 PTp51(156) | AGTGGTAATGGCCGTGAC | 11 | FAM | TaqMan MGB | HPV51 |
| 2 PTp51(158) | TGGTAATGGCCGTGACC | 37 | FAM | TaqMan MGB | HPV51 |
| 2 PTp51(168) | CGTGACCCTATAGAAAG | 38 | FAM | TaqMan MGB | HPV51 |
| 2 PTp 56 | TAG CAA TGG TAG AGA AC | 39 | VIC | TaqMan MGB | HPV56 |
| 2 PTp56(2) | CAATACCTGCAGAGTTATA | 12 | VIC | TaqMan MGB | HPV56 |
| 2 PTp56(3) | ATATTTAAAGGGTAGCAATGGT | 41 | VIC | TaqMan MGB | HPV56 |
| 2 PTp 66(1) | TTG AAA GGG TGG CAA T | 13 | NED | TaqMan MGB | HPV66 |
| 3 PTp 16(6) | ATT TGC AGT AGA CCC AGA G | 14 | FAM | TaqMan MGB | HPV16 |
| 3 PTp16(94) | CTGTTGGTGAAAATGTACC | 44 | FAM | TaqMan MGB | HPV16 |

TABLE 2-continued

List of probes

| GrpHPV | Sequence | SEQ ID NO | Label | Type | Target |
|---|---|---|---|---|---|
| 3 PTp16(101) | TGAAAATGTACCAGACGATT | 45 | FAM | TaqMan MGB | HPV16 |
| 3 PTp16(155s) | AGCCAGTTCAAATTAT | 46 | FAM | TaqMan MGB | HPV16 |
| 3/4PTp 33 | TCT ATT CAA AGC AGT GC | 47 | VIC | TaqMan MGB | HPV33 |
| 3/4PTp33(2) | ctac+Tgc+Ctc+Ta+Tt+Ca+Aag+Cag | 48 | ROX/BHQ2 | LNA | HPV33 |
| 3/4PTp33(8) | TGCCTCTATTCAAAGCAGTGC | 49 | NED, VIC | TaqMan MGB | HPV33 |
| 3/4PTp33(10) | GGAACTACTGCCTCTATTCAAAGCAGTGCTGC | 50 | VIC | TaqMan | HPV33 |
| 3/4PTp33(141) | AGAGGCTGTTCCCGATGACCTG | 51 | ROX | TaqMan | HPV33 |
| 3/4PTp33(149) | TTCCCGATGACCTGTACATTAAAGGT | 52 | ROX | TaqMan | HPV33 |
| 3/4PTp33(9) | tg+Cctctatt+Caaag+Cagtgc | 19 | ROX/BHQ2 | LNA | HPV33 |
| 3 PTp 58 | TCC GGT AAT ACT GCA G | 16 | NED | TaqMan MGB | HPV58 |
| 3 PTp58(36) | CCAGTGAACCTTATGGG | 55 | NED | TaqMan MGB | HPV58 |
| 3 PTp58(118 m) | AAAACTTGGCGAGGCTG | 56 | NED | TaqMan MGB | HPV58 |
| 3 PTp58(156) | AAGGGTCCGGTAATAC | 57 | NED | TaqMan MGB | HPV58 |
| 3 PTp58(170) | ACTGCAGTTATCCAAAGTA | 58 | NED | TaqMan MGB | HPV58 |
| 3/1PTp 45(3) | ATA CAC ACA ACT GCC A | 59 | VIC | TaqMan MGB | HPV45 |
| 3/1PTp45(6) | GTGAAACCCCTGGCAGT | 15 | VIC | TaqMan MGB | HPV45 |
| 3/1PTP45(4) | aa+Tac+Aca+Caa+Ctg+Ccagg | 61 | ROX/BHQ2 | LNA | HPV45 |
| 3/1PTp45(5) | ct+Agc+Gct+Aat+Atg+Cgtgaa | 62 | ROX/BHQ2 | LNA | HPV45 |
| 3/1PTp45(172Q) | TGCGTGAAACCCCTGGCAGTTG | 63 | VIC | TaqMan | HPV45 |
| 3/1PTp45(127) | ACACAGTACCTACGGACCTA | 64 | VIC | TaqMan MGB | HPV45 |
| 3/1PTp45(164) | CGCTAATATGCGTGAAAC | 65 | VIC | TaqMan MGB | HPV45 |
| 4 PTp 35 | TAC CAC TGG CAC ATT G | 66 | FAM | TaqMan MGB | HPV35 |
| 4 PTp35(4) | GTACCACTGGCACATTG | 20 | FAM | TaqMan MGB | HPV35 |
| 4 pTP35(5) | TACCACTGGCACATTG | 68 | FAM | TaqMan MGB | HPV35 |
| 4 PTp 31 | TCC GGT TCA ACA GCT AC | 18 | VIC | TaqMan MGB | HPV31 |
| 4 PTp31 (115g) | TCAGGCGCGGTTGGTGAATCGGT | 70 | VIC | TaqMan | HPV31 |

TABLE 2-continued

List of probes

| GrpHPV | Sequence | SEQ ID NO | Label | Type | Target |
|---|---|---|---|---|---|
| 4 PTp31(168) | TTCAACAGCTACTTTAGC | 71 | VIC | TaqMan MGB | HPV31 |
| 4 PTp31(162) | CTCCGGTTCAACAGCTA | 72 | VIC | TaqMan MGB | HPV31 |
| 4 PTp6(2) | TGCCTGATACTCTTATAATTAA | 73 | NED | TaqMan MGB | HPV6 |
| 4 PTp6(197) | ACCCCGAGCGGCT | 74 | NED | TaqMan MGB | HPV6 |
| 4 PTp6(190) | TGTTAACACCCCGAGCGG | 75 | NED | TaqMan MGB | HPV6 |
| 4 PTp6(154) | TAGTGGAAATCGCACGTCT | 17 | NED | TaqMan MGB | HPV6 |
| 4 PTp6(101) | AACAGGGCTGGCGAGGTGGG | 77 | ROX/BHQ2 | TaqMan | HPV6 |
| 4 PTp6(98) | TTTAACAGGGCTGGCGAGGTGGG | 78 | ROX/BHQ2 | TaqMan | HPV6 |
| 4 PTp6(122) | ACAGGGCTGGCGAGGTGGG | 79 | ROX/BHQ2 | TaqMan | HPV6 |
| 4 PTp6(116) | TTTTTAACAGGGCTGGCGAGGT | 80 | ROX/BHQ2 | TaqMan | HPV6 |

The multiplex group to which the types are currently assigned is given in the first column. Locked nucleic acid (LNA™) sequences are written with lower case letters for normal residues and uppercase letters prefixed with '+' for LNA residues. Probes in use in the multiplex mixes shown below are in bold text. Grey text indicates that the probe has been replaced. The fluorophors used (FAM, VIC, NED and ROX) are those used in the present method. Alternative fluorophors and combinations of fluorophors may be used as known by the skilled man.

After 1-3 rounds of probe/primer redesign, the multiplex formulation in Table 3 was arrived at.

TABLE 3

Composition of the Multiplex PCR mixes

Multiplex Group 1. HPV 18,52,59.

| Primer | Sequence | SEQ ID NO | Concentration |
|---|---|---|---|
| PTf | 5-TG(CT)AAA TAT CC(AT) GAT TAT (AT)TI IAA ATG-3 | 1 | 600 nM |
| PTrGr1b | 5-TGT AGC CAG TAT GG(CT) TTA TTG AA-3 | 2 | 600 nM |

| Probe | Sequence | SEQ ID NO | Type | Concentration |
|---|---|---|---|---|
| PTp18(131) | 5- FAM ACT GTG CCT CAA TCC-3 | 7 | TaqMan MGB | 150 nM |
| PTp52(4) | 5- ROX TC+TAA+CTC+TGGC+AA+TAC+TGC-3 | 8 | LNA | 50 nM |
| PTp59(1) | 5- NED TAC TGA CAT ACG TGC C-3 | 9 | TaqMan MGB | 100 nM |

Multiplex Group 2. HPV 39,51,56,66

| Primer | Sequence | SEQ ID NO | Concentration |
|---|---|---|---|
| PTf | 5-TG(CT)AAA TAT CC(AT) GAT TAT (AT)TI IAA ATG-3 | 1 | 600 nM |
| PTrGr2 | 5-TG(GT) AGC CAA TAA GGT TTA TTA AA-3 | 3 | 600 nM |

TABLE 3-continued

Composition of the Multiplex PCR mixes

| Probe | Sequence | SEQ ID NO | Type | Concentration |
|---|---|---|---|---|
| PTp 39(4) | 5-ROX CA+CA+GATAT+ACG+TG+CAA+ACC-3 | 10 | LNA | 50 nM |
| PTp 51(156) | 5- FAM AGT GGT AAT GGC CGT GAC-3 | 11 | TaqMan MGB | 100 nM |
| PTp 56(2) | 5- VIC CAA TAC CTG CAG AGT TAT A-3 | 12 | TaqMan MGB | 50 nM |
| PTp 66 (1) | 5- NED TTG GAA GGG TGG CAA T-3 | 13 | TaqMan MGB | 100 nM |

Multiplex Group 3. HPV 16,45,58

| Primer | Sequence | SEQ ID NO | Concentration |
|---|---|---|---|
| PTf | 5-TG(CT)AAA TAT CC(AT) GAT TAT (AT)TI IAA ATG-3 | 1 | 600 Nm |
| PTr957 | 5- TGI AIC CAA TAI GG(CT) TTA TTG AA -3 | 4 | 600 Nm |

| Probe | Sekvens | SEQ ID NO | Type | Concentration |
|---|---|---|---|---|
| PTp16(6) | 5- FAM ATT TGC AGT AGA CCC AGA G-3 | 14 | TaqMan MGB | 150 Nm |
| PTp45(6) | 5- VIC GTG MA CCC CTG GCA GT-3 | 15 | TaqMan MGB | 150 Nm |
| PTp58 | 5- NED TCC GGT AAT ACT GCA G-3 | 16 | TaqMan MGB | 50 Nm |

Multiplex Group 4. HPV 6,31,33,35

| Primer | Sequence | SEQ ID NO | Concentration |
|---|---|---|---|
| Oli1+ | 5- TG(CT)AAA TAT CC(AT)_ATT AT (AT)TI IAA ATG -3 | 1 | 600 nM |
| PTrGr4 | 5- TGT AIC CAA TAT GGt TTA TTA AA-3 | 5 | 600 nM |

| Probe | Sekvens | SEQ ID NO | Kons.i Quantamix | C.off |
|---|---|---|---|---|
| PTp 6(154) | 5-TAG TGG AAA TCG CAC GTC T- 3 NED | 17 | 50 nM | 6-7 |
| PTp 31 | 5-TCC GGT TCA ACA GCT AC-3 VIC | 18 | 50 nM | 31-9 |
| PTp 33(9) | 5-ROX tg(+C)ctctatt(+C)aaag(+C) agtgc-BHQ2 | 19 | 150 nM | 33-7 |
| PTp 35(4) | 5- GTA CCA CTG GCA CAT TG-3 FAM | 20 | 100 nM | 35-7 |

Example 10

Internal Control

A plasmid containing the genome of the non-oncogenic HPV type HPV6 was used as an internal control. Design and testing of the HPV6 internal control probe was as for the other probes. In order to determine a suitable concentration of internal control, HPV6 was added to group 4 PCR reactions at 10× serially diluted concentrations from $4.10^3$ GU to 40 GU per reaction. The multiplex mix containing internal control was used in amplification test using HPV types 31, 33 and 35 10× dilution series in order to determine which internal control concentrations, if any, reduced analytical sensitivity for the target types.

Example 11

Evaluation Against Clinical Samples

Once the final formulation of the test was arrived at based on the results of the above tests, the test was evaluated on 37 clinical specimens and the results were compared with the previous results of the hybrid capture HCII test and previous typing results using a reverse line-blot test.

Table 4 compares the results of consensus multiplex PCR for 37 clinical samples, compared with the hybrid capture (HCII) test and the results of previous typing using reversed line blot. No false negative results relative to the previous tests were encountered. One sample was false negative relative to the HCII test and in one sample the consensus multiplex test failed to detect a type found by the previous typing test.

The results thus shows that in 5 samples the consensus multiplex test according to the present invention detected additional types not detected in the previous analyses.

TABLE 4

Evaluation of Consensus Realtime Test on Clinical Samples

| Sample | Result HCII | Previous Typing Result | Result Consensus Multiplex |
|---|---|---|---|
| 1 | + | HPV16 | HPV16 |
| 2 | − | − | − |
| 3 | − | − | − |
| 4 | + | HPV35 | HPV16, 35, 52 |
| 5 | − | − | − |
| 6 | + | HPV31 | HPV31, 52 |
| 7 | − | − | − |
| 8 | + | HPV51 | HPV51, 56 |
| 9 | + | HPV51 | HPV51 |
| 10 | − | − | − |
| 11 | − | − | − |
| 12 | − | − | HPV51, 66 |
| 13 | − | − | − |
| 14 | − | − | − |
| 15 | − | − | − |
| 16 | − | − | − |
| 17 | − | − | − |
| 18 | + | HPV39 | HPV39 |
| 19 | − | − | − |
| 20 | − | HPV51 | HPV51 |
| 21 | − | − | HPV16, 45 |
| 22 | − | − | − |
| 23 | − | − | − |
| 24 | − | − | − |
| 25 | − | − | − |
| 26 | + | − | − |
| 27 | − | − | − |
| 28 | − | − | − |
| 29 | − | − | − |
| 30 | ± | HPV45 | HPV45 |
| 31 | − | − | − |
| 32 | + | HPV16 | HPV16 |
| 33 | − | − | − |
| 34 | − | HPV31 | HPV31 |
| 35 | + | HPV51, 52, 59 | HPV51, 52 |
| 36 | − | − | − |
| 37 | − | − | − |

Table 4 thus compares the results of consensus multiplex PCR for 37 clinical samples, compared with the HCII test and the results of previous typing using reversed line blot. There was complete agreement of results for 28 samples, of which five were positive and 23 were negative. For two samples HCII was negative while reverse line blot and consensus multiplex PCR gave identical results. In 5 samples the consensus multiplex test detected extra types not detected by reverse lineblot. These types were HPV66 (one sample), which is not included in the reverse line blot assay, HPV52 (two samples) and HPV56 (one sample) for which the reverse line blot assay is known to have reduced sensitivity and HPV35, HPV16 and HPV45 (one case each). In one sample the consensus multiplex test failed to detect a type (HPV59) detected by reverse line blot. One sample was positive only by the HCII test.

Example 12

Consensus Realtime PCR Setup

The following procedure was used to analyse 21 clinical samples. The samples were DNA from cervical brush samples extracted using the MagNAPure automatic DNA extractor.

1. PCR mixes for multiplex groups 1, 2, 3 and 4 were prepared in separate tubes according to the tables below.

TABLE 5

HPV Group 1, mastermix formulation: 50 μl reaction.
Primer concentration 600 nM.
Probe concentration 150 nM for HPV18, 50 nM for HPV52 and 100 nM for HPV59.

| Component | Volume Per sample | Volume 26 samples and controls |
|---|---|---|
| Rx-mix QuantaFast Cycling qPCR | 25 μl | 650 μl |
| PTf 100 pmol/μl | 0.3 μl | 7.8 μl |
| PtrGr1 100 pmol/μl | 0.3 μl | 7.8 μl |
| Probes 18(131), 52(4), 59(1) 5 pmol/μl | 1.5 + 0.5 + 1.0 μl | 39 + 13 + 26 μl |

TABLE 6

HPV Group 2, mastermix formulation: 50 μl reaction.
Primer concentration 600 nM.
Probe concentration 50 nM for HPV39, 100 nM for HPV51, 50 nM for HPV56 and 100 nM for HPV66

| Component | Volume Per sample | Volume 26 samples and controls |
|---|---|---|
| Rx-mix QuantaFast Cycling qPCR | 25 μl | 650 μl |
| PTf 100 pmol/μl | 0.3 μl | 7.8 μl |
| PTrGr2 100 pmol/μl | 0.3 μl | 7.8 μl |
| Probes 39(4), 51(156), 56(2)66(1) 5 pmol/μl | 0.5 + 1.0 + 0.5 + 1.0 μl | 13 + 26 + 13 + 26 μl |
| $H_2O$ | 16.4 μl | 426 μl |

TABLE 7

HPV Group 3, mastermix formulation: 50 μl reaction.
Primer concentration 600 nM.
Probe concentration 150 nM for HPV16, 150 nM for HPV45 and 50 nM for HPV58

| Component | Volume Per sample | Volume 26 samples and controls |
|---|---|---|
| Rx-mix QuantaFast Cycling qPCR | 25 μl | 650 μl |
| PTf 100 pmol/μl | 0.3 μl | 7.8 μl |
| PTr 100 pmol/μl | 0.3 μl | 7.8 μl |
| Probes 16(6), 45(6), 58 5 pmol/μl | 1.5 + 1.5 + 0.5 μl | 39 + 39 + 13 μl |
| $H_2O$ | 15.9 μl | 413 μl |

TABLE 8

HPV Group 4, mastermix formulation: 50 µl reaction.
Primer concentration 600 nM.
Probe concentration 50 nM for HPV6, 50 nM for HPV31,
150 nM for HPV33 and 100 nM for HPV35

| Component | Volume Per sample | Volume 26 samples and controls |
|---|---|---|
| Rx-mix QuantaFast Cycling qPCR | 25 µl | 650 µl |
| PTf 100 pmol/µl | 0.3 µl | 7.8 µl |
| PtrGr 4 100 pmol/µl | 0.3 µl | 7.8 µl |
| Probes 6(154), 31, 33(9), 35(4) 5 pmol/µl | 0.5 + 0.5 + 1.5 + 1.0 µl | 13 + 13 + 39 + 26 µl |
| IK | 0.5 µl | 13 µl |
| H$_2$O | 15.9 µl | 413 µl |

2. PCR program: 95° C., 12 min followed by 45 cycles of 95° C., 15 s; 45° C., 30 s; 60° C., 60 s. AB7300 realtime PCR machine. The following 96 well plate setup is used:

Rows 1, 2, 3: detectors for Group 1,
Rows 4, 5, 6: detectors for Group 2,
Rows 7, 8, 9 detectors for Group 3 and
Row 10, 11, 12 detectors for Group 4.
Sample number for each of the 21 samples is also entered.
Each sample is run in all groups. In addition, group specific control mixes containing all the HPV types in the group and negative controls are included.

Thus the following controls are included:

Positive Controls 13-type control, containing 4000 GU of HPV16, 18, 31, 33, 35, 39, 45, 51, 52, 56, 58, 59 and 66 per 5 µl aliquot.

Group positive controls, containing 4000 GU of HPV18, 52 and 59 (group 1), HPV39, 51, 59 and 66 (group 2), HPV16, 45 and 58 (group 3) and HPV 31, 33 and 35 (group 4) were used with their respective groups.

For each multiplex group a 13-type multiplex control, a group control and a negative control (no DNA added) were run.

3. PCR mixes as described in (1) are aliquoted, 45 µl to a well, following the plate setup.

5 µl sample DNA, positive control or negative control are added according to the plate setup.

The PCR plate is sealed and placed in the PCR machine. The PCR program takes approximately 2.5 hours.

Logistic Considerations

The time required for completion of the analysis of 20 samples is 8 hours—4.5 hours for sample processing, 15 minutes for PCR setup, 2.5 hours PCR run time and 1 hour for analysis. Of this, 2.5 hours is hands-on time.

Analysis of samples and amplification curves for consensus multiplex realtime PCR type for the specific detection of HPV types 16, 18, 31, 33, 35, 39, 45, 51, 52, 56, 58, 59 and 66 are shown in FIGS. 1-13. The vertical axis is log (fluorescence), background subtracted, for the appropriate colour channel. The horizontal axis is PCR cycle. The horizontal line marked with an arrowhead on the right hand vertical axis is the threshold line which is placed manually after correction for background fluoresence. Amplification curves crossing the threshold line are considered positive, and the fractional PCR cycle where the amplification curve crosses the threshold line is the threshold cycle ($C_T$) given in the accompanying report. FIG. 4 shows amplification of the internal control, HPV6.

Results for Multiplex Group 1. HPV18, 52 and 59.

FIG. 1 shows amplification of HPV18 in multiplex group 1. The two positive curves are positive controls. There are no HPV18-positive samples.

FIG. 2 shows amplification of HPV52 in multiplex group 1. 4 positive curves are visible. The orange and grey curves to the right are positive controls. The two blue curves are positive samples (samples four and 6) containing HPV52.

FIG. 3 shows amplification of HPV59 in multiplex group 1. The two positive curves are positive controls. There are no HPV59-positive samples.

Results for Multiplex Group 2. HPV39, 51, 56 and 66.

FIG. 4 shows amplification of HPV39 in multiplex group 2. The green curve is a positive control containing the target types of group 2. In a second positive control containing all fourteen target types HPV39 failed to amplify. The black curve is a strongly positive sample (sample 18) containing HPV39.

FIG. 5 shows amplification of HPV51 in multiplex group 2. Six positive curves are visible. The green and brown curves crossing the threshold line at cycle 29 are positive controls. The four remaining curves are HPV51-positive samples, two of which (samples 8 and 9 are very strongly positive). The black and blue curves for these two samples are almost coincident. Sample 20 (green curve) crosses the threshold line close to the positive controls, indicating that it contains similar amounts of HPV51 (4000 GU). Sample 12 (red curve) is weakly positive.

FIG. 6 shows amplification of HPV56 in multiplex group 2. 3 positive curves are visible. Green and brown curves are positive controls. The blue curve is a positive sample (sample 8). The flattened curve is due to the competitive effect of the very high concentrations of HPV51 in this sample.

FIG. 7 shows amplification of HPV66 in multiplex group 2. The green and brown positive curves at the extreme right are positive controls. The red curve is a positive sample.

Results for Multiplex Group 3. HPV16, 45 and 58.

FIG. 8 shows amplification of HPV16 in multiplex group 3. 4 positive curves are visible. The brown and red curves crossing the threshold line at cycle 34 are positive controls. The brown curve is noticeably flatter than the red curve, probably because the positive control represented by the brown curve contains all fourteen target types, producing a greater potential for competition. The black and green curves are HPV16-positive samples (samples 1 and 21) one of which is very weakly positive.

FIG. 9 shows amplification of HPV45 in multiplex group 3. 3 positive curves are visible. The brown and red curves are positive controls. The green curve is an HPV45 positive sample (sample 21).

FIG. 10 shows amplification of HPV58 in multiplex group 3. The two positive curves are positive controls. There are no HPV58-positive samples.

Results for Multiplex Group 4. HPV31, 33, 35 and Internal Control (HPV6)

FIG. 11 shows amplification of HPV31 in multiplex group 4. 3 positive curves are visible. The two similar green curves are positive controls. The blue curve is a positive sample (sample 6) containing large amounts of HPV31.

FIG. 12 shows amplification of HPV33 in multiplex group 4. The two similar green curves are positive controls which are the only positive signals. There are no HPV33-positive samples.

FIG. 13 shows amplification of HPV35 in multiplex group 4. 3 positive curves are visible. The two similar green curves are positive controls. The maroon curve is a positive sample (sample 4) containing HPV35.

FIG. 14 shows internal control amplification curves. The samples all contain the same amount of HPV6 and the curves are clustered, indicating absence of inhibition. The curves to the right of the main cluster of curves are indicative of partial inhibition or competition. Five such curves are seen. In one curve (sample 4) the amplification of the internal control is nearly completely inhibited. This is caused by competition with a strong HPV35 amplification signal in the same tube. A second slightly inhibitory sample, sample 9, contains HPV51 at unusually high concentrations. Although HPV51 is not included in multiplex group 4, the similarity of the primer sequences is probably sufficient to generate a competitive amplification in such a hot sample. The remaining three samples (3, 8 and 17) are negative and are probably partially inhibitory.

The internal control, HPV6 could thus be added to the group 4 multiplex reaction at levels of 400-4000 GU per reaction without compromising the analytical sensitivity for HPV31, HPV33 or HPV35. 4000 GU per reaction was chosen as standard concentration for the internal control.

TABLE 9

Analytical sensitivity

| HPV type | Analytical sensitivity (GU) (100 ng/μl human DNA) | Analytical sensitivity (GU) (10 ng/μl human DNA) |
| --- | --- | --- |
| HPV16 | 40 | 4 |
| HPV18 | 40 | 4 |
| HPV31 | 4 | 4 |
| HPV33 | 400 | 40 |
| HPV35 | 400 | 40 |
| HPV39 | 40 | 4 |
| HPV45 | 400 | 4 |
| HPV51 | 4 | 4 |
| HPV52 | 400 | 40 |
| HPV56 | 40 | 4 |
| HPV58 | 400 | 40 |
| HPV59 | 40 | 4 |
| HPV66 | 400 | 40 |

This table refers to the analytical sensitivity for multiplex PCR reactions. Reactions were performed using the multiplex formulations described in tables 5-8. Target DNA was a 10 fold serial dilution of HPV plasmid in 100 ng/μl or 10 ng/μl human DNA, corresponding to 500 or 50 ng respectively of human DNA in the sample. The analytical sensitivity is the lowest number of copies (GU) that gives an amplification curve that can be clearly distinguished from background fluoresence.

Example 13

Use of Primer PTr2

Amplification was performed with dilution series of HPV16, HPV18, HPV31, HPV33, HPV35 and HPV56 with primers PTf and PTr2.

The amplification was thus performed in a 100 μl reaction using 500 ng of each primer, 1.5 u Amplitaq Gold (Applied Biosystems), 1.5 mM $MgCl_2$, and 200 μM dNTPs in Amplitaq Gold buffer. The PCR program was 93° C., 30 s; 40° C., 30 s; 72° C., 90 s; 40 cycles. 10 μl of the amplified material was applied to a 1.5% agarose gel and subjected to electrophoresis at 130 V for 90 minutes, stained with SYBR green according to the manufacturers instructions and photographed under 300 nm UV illumination. The results are shown in FIGS. 15-22.

PTr2 is thus suitable for the amplification of HPV types.

Example 14

Diagnostic Kit

The diagnostic kit according to the present invention may have the following construction, but it is obvious that various changes and modifications may be effected by one skilled in the art without departing from the scope or spirit of the invention.

The kit may contain four rows of six tubes (Tubes 1-6) containing all the reagents necessary for detection of HPV types 16, 18, 31, 33, 35, 39, 45, 51, 52, 56, 58, 59 and 66.

Tube 1 contains 500 μl of a solution containing forward primer PTf and reverse primer PTrGr1, plus TaqMan MGB probes for HPV18 (FAM label), HPV59 (NED label) and an LNA probe for HPV52 (ROX label).

Tube 2 contains 500 μl of a solution containing forward primer PTf and reverse primer PTrGr2, plus TaqMan MGB probes for HPV51 (FAM label), HPV56 (VIC label) HPV66 (NED label) and an LNA probe for HPV39 (ROX label).

Tube 3 contains 500 μl of a solution containing forward primer PTf and reverse primer PTr, plus TaqMan MGB probes for HPV16 (FAM label), HPV45 (VIC label) and HPV58 (NED label)

Tube 4 contains 500 μl of a solution containing forward primer PTf and reverse primer PTrGr4, plus TaqMan MGB probes for HPV35 (FAM label), HPV31 VIC label, and an LNA probe for HPV52 (ROX label). Also included is a TaqMan probe for the HPV6 internal control and HPV6 internal control target at a concentration of 800 copies per μl.

Tube 5 contains 20 μl of positive control containing 4000 copies of HPV types 16, 18, 31, 33, 35, 35, 39, 45, 51, 52, 56, 58, 59 and 66.

Tube 6 contains 2500 μl of 2×PCR mastermix containing thermostable DNA polymerase and deoxynucleotide triphosphates and magnesium chloride in a proprietary buffer solution.

According to the following procedure 23 samples may be analysed simultaneously. Three of these samples may be negative controls. Further, DNA is extracted from the samples using a suitable method.

1. Each of tubes 1 to 6 are allowed to thaw at room temperature.
2. Group 1 mastermix of example 12 is prepared by adding 600 μl of PCR mastermix (tube 6) to tube 1 and mixed by inversion.
3. Group 2 mastermix of example 12 is prepared by adding 600 μl of PCR mastermix (tube 6) to tube 2 and mixed by inversion.
4. Group 3 mastermix of example 12 is prepared by adding 600 μl of PCR mastermix (tube 6) to tube 3 and mixed by inversion.
5. Group 4 mastermix of example 12 is prepared by adding 600 μl of PCR mastermix (tube 6) to tube 4 and mixed by inversion.
6. 45 μl of group 1 mastermix is transferred to each well of rows A and E of a 96-well 500 μl optical PCR plate.
7. 45 μl of group 2 mastermix is transferred to each well of rows B and F.
8. 45 μl of group 3 mastermix is transferred to each well of rows C and G.
9. 45 μl of group 4 mastermix to each well of rows D and H.
10. Add 5 μl of sample DNA 1 to wells A1, B1, C1 and D1.
11. Add 5 μl of sample DNA 2 to wells A2, B2, C2 and D2.

12. Continue adding samples in the same pattern to wells A3-D3 through A12-D12.
13. Continue adding samples in the same pattern to wells D1-H1 through D11-H11.
14. Add 5 μl of positive control to each of wells D12-H12.
15. Seal the plate, place in the realtime PCR machine and start the PCR program.
16. HPV types 18, 52 and 59 will be detected in rows A and E.
17. HPV types 39, 51, 56 and 66 will be detected in rows B and F.
18. HPV types 16, 45 and 58 will be detected in rows C and G.
19. HPV types 31, 33, 35 and the internal control will be detected in rows D and H.

The PCR program should be:
Polymerase activation and sample denaturation: 10 mins at 95° C.
Followed by 45 cycles of:
Denaturation 15 seconds at 95° C.
Annealing 30 seconds at 45° C.
Extension 60 seconds at 60° C.

The realtime PCR machine should be programmed to collect fluorescence data in four colour channels optimized for detection of the fluorescent dyes FAM, VIC, NED and ROX.

The above Examples are only meant as illustrating the invention. It must be understood that a person skilled in the art can modify the method, kit, probes and primers herein described without deviating from the concept and scope of this invention set forth in the claims.

The invention claimed is:

1. A method for simultaneously detecting and/or typing and/or quantifying HPV 18, 52, 59, 39, 51, 56, 66, 16, 45, 58, 31, 33 and 35 in a biological sample, the method comprising the following four parallel reactions:

Reaction 1
- a) amplification of nucleic acid fragments of HPV 18, 52 and 59 in the presence of
  - (i) a nucleic acid polymerase
  - (ii) a forward PCR primer with the oligonucleotide sequence of SEQ ID NO: 1,
  - (iii) a reverse PCR primer with the oligonucleotide sequence of SEQ ID NO: 2, and
  - (iv) probes comprising SEQ ID NO: 7, 8 and 9, each labelled with a different fluorophore and a quencher molecule; and
- b) detecting a change in fluorescence, the wavelengths and magnitude thereof determining the quantity and/or presence of HPV type 18, 52 and 59;

Reaction 2
- a) amplification of nucleic acid fragments of HPV 39, 51, 56 and 66 in the presence of
  - (i) a nucleic acid polymerase
  - (ii) a forward PCR primer with the oligonucleotide sequence of SEQ ID NO: 1,
  - (iii) a reverse PCR primer with the oligonucleotide sequence of SEQ ID NO: 3, and
  - (iv) probes comprising SEQ ID NO: 10, 11, 12 and 13, each labelled with a different fluorophore and a quencher molecule; and
- b) detecting a change in fluorescence, the wavelengths and magnitude thereof determining the quantity and/or presence of HPV type 39, 51, 56 and 66;

Reaction 3
- a) amplification of nucleic acid fragments of HPV 16, 45 and 58 in the presence of
  - (i) a nucleic acid polymerase
  - (ii) a forward PCR primer with the oligonucleotide sequence of SEQ ID NO: 1,
  - (iii) a reverse PCR primer with the oligonucleotide sequence of SEQ ID NO: 4, and
  - (iv) probes comprising SEQ ID NO: 14, 15 and 16, each labelled with a different fluorophore and a quencher molecule; and
- b) detecting a change in fluorescence, the wavelengths and magnitude thereof determining the quantity and/or presence of HPV type 16, 45 and 58; and Reaction 4
- a) amplification of nucleic acid fragments of HPV 31, 33 and 35 and an internal control in the presence of
  - (i) a nucleic acid polymerase
  - (ii) a forward PCR primer with the oligonucleotide sequence of SEQ ID NO: 1,
  - (iii) a reverse PCR primer with the oligonucleotide sequence of SEQ ID NO: 5,
  - (iv) probes comprising SEQ ID NO: 17, 18, 19 and 20, each labelled with a different fluorophore and a quencher molecule; and
  - (v) an internal control; and
- b) detecting a change in fluorescence, the wavelengths and magnitude thereof determining the quantity and/or presence of HPV type 31, 33, 35.

2. The method according to claim 1, wherein Reactions 1-4 are performed in parallel and in separate vials.

3. The method according to claim 1, wherein the fluorophores are FAM, VIC, NED and ROX.

4. The method according to claim 2, wherein the fluorophores are FAM, VIC, NED and ROX.

5. The method according to claim 1, wherein the internal control is HPV6.

6. The method according to claim 2, wherein the internal control is HPV6.

* * * * *

```
                       SEQUENCE LISTING

<160> NUMBER OF SEQ ID NOS: 80

<210> SEQ ID NO 1
<211> LENGTH: 27
<212> TYPE: DNA
<213> ORGANISM: Human papillomavirus
<220> FEATURE:
<221> NAME/KEY: modified_base
<222> LOCATION: (21)..(22)
<223> OTHER INFORMATION: I
<220> FEATURE:
<221> NAME/KEY: misc_feature
<222> LOCATION: (21)..(22)
<223> OTHER INFORMATION: n is a, c, g, or t

<400> SEQUENCE: 1
tgyaaatatc cwgattatwt nnaaatg                                          27

<210> SEQ ID NO 2
<211> LENGTH: 23
<212> TYPE: DNA
<213> ORGANISM: Human papillomavirus

<400> SEQUENCE: 2
tgtagccagt atggyttatt gaa                                              23

<210> SEQ ID NO 3
<211> LENGTH: 23
<212> TYPE: DNA
<213> ORGANISM: Human papillomavirus

<400> SEQUENCE: 3
tgkagccaat aaggtttatt aaa                                              23

<210> SEQ ID NO 4
<211> LENGTH: 23
<212> TYPE: DNA
<213> ORGANISM: Human papillomavirus
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (5)..(5)
<223> OTHER INFORMATION: I
<220> FEATURE:
<221> NAME/KEY: misc_feature
```

```
<222> LOCATION: (5)..(5)
<223> OTHER INFORMATION: n is a, c, g, or t
<220> FEATURE:
<221> NAME/KEY: modified_base
<222> LOCATION: (12)..(12)
<223> OTHER INFORMATION: I
<220> FEATURE:
<221> NAME/KEY: misc_feature
<222> LOCATION: (12)..(12)
<223> OTHER INFORMATION: n is a, c, g, or t

<400> SEQUENCE: 4
tgnanccaat anggyttatt gaa                                           23

<210> SEQ ID NO 5
<211> LENGTH: 23
<212> TYPE: DNA
<213> ORGANISM: Human papillomavirus
<220> FEATURE:
<221> NAME/KEY: modified_base
<222> LOCATION: (5)..(5)
<223> OTHER INFORMATION: I
<220> FEATURE:
<221> NAME/KEY: misc_feature
<222> LOCATION: (5)..(5)
<223> OTHER INFORMATION: n is a, c, g, or t

<400> SEQUENCE: 5
tgtanccaat atggtttatt aaa                                           23

<210> SEQ ID NO 6
<211> LENGTH: 26
<212> TYPE: DNA
<213> ORGANISM: Human papillomavirus
<220> FEATURE:
<221> NAME/KEY: modified_base
<222> LOCATION: (11)..(11)
<223> OTHER INFORMATION: I
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(15)
<223> OTHER INFORMATION: n is a, c, g, or t

<400> SEQUENCE: 6
ckgtrgtatc nccancaagt aacaaa                                        26

<210> SEQ ID NO 7
<211> LENGTH: 15
<212> TYPE: DNA
<213> ORGANISM: Human papillomavirus

<400> SEQUENCE: 7
actgtgcctc aatcc                                                    15

<210> SEQ ID NO 8
<211> LENGTH: 20
<212> TYPE: DNA
<213> ORGANISM: Human papillomavirus
<220> FEATURE:
<221> NAME/KEY: modified_base
<222> LOCATION: (3)..(3)
<223> OTHER INFORMATION: LNA residue
<220> FEATURE:
```

```
<221> NAME/KEY: modified_base
<222> LOCATION: (6)..(6)
<223> OTHER INFORMATION: LNA residue
<220> FEATURE:
<221> NAME/KEY: modified_base
<222> LOCATION: (9)..(9)
<223> OTHER INFORMATION: LNA residue
<220> FEATURE:
<221> NAME/KEY: modified_base
<222> LOCATION: (13)..(13)
<223> OTHER INFORMATION: LNA residue
<220> FEATURE:
<221> NAME/KEY: modified_base
<222> LOCATION: (15)..(15)
<223> OTHER INFORMATION: LNA residue
<220> FEATURE:
<221> NAME/KEY: modified_base
<222> LOCATION: (18)..(18)
<223> OTHER INFORMATION: LNA residue

<400> SEQUENCE: 8
tctaactctg gcaatactgc                                               20

<210> SEQ ID NO 9
<211> LENGTH: 16
<212> TYPE: DNA
<213> ORGANISM: Human papillomavirus

<400> SEQUENCE: 9
tactgacata cgtgcc                                                   16

<210> SEQ ID NO 10
<211> LENGTH: 20
<212> TYPE: DNA
<213> ORGANISM: Human papillomavirus
<220> FEATURE:
<221> NAME/KEY: modified_base
<222> LOCATION: (3)..(3)
<223> OTHER INFORMATION: LNA residue
<220> FEATURE:
<221> NAME/KEY: modified_base
<222> LOCATION: (5)..(5)
<223> OTHER INFORMATION: LNA residue
<220> FEATURE:
<221> NAME/KEY: modified_base
<222> LOCATION: (10)..(10)
<223> OTHER INFORMATION: LNA residue
<220> FEATURE:
<221> NAME/KEY: modified_base
<222> LOCATION: (13)..(13)
<223> OTHER INFORMATION: LNA residue
<220> FEATURE:
<221> NAME/KEY: modified_base
<222> LOCATION: (15)..(15)
<223> OTHER INFORMATION: LNA residue
<220> FEATURE:
<221> NAME/KEY: modified_base
<222> LOCATION: (18)..(18)
<223> OTHER INFORMATION: LNA residue

<400> SEQUENCE: 10
cacagatata cgtgcaaacc                                               20

<210> SEQ ID NO 11
<211> LENGTH: 18
<212> TYPE: DNA
<213> ORGANISM: Human papillomavirus

<400> SEQUENCE: 11
agtggtaatg gccgtgac                                                 18
```

```
<210> SEQ ID NO 12
<211> LENGTH: 19
<212> TYPE: DNA
<213> ORGANISM: Human papillomavirus

<400> SEQUENCE: 12
caatacctgc agagttata                                               19

<210> SEQ ID NO 13
<211> LENGTH: 16
<212> TYPE: DNA
<213> ORGANISM: Human papillomavirus

<400> SEQUENCE: 13
ttggaagggt ggcaat                                                  16

<210> SEQ ID NO 14
<211> LENGTH: 19
<212> TYPE: DNA
<213> ORGANISM: Human papillomavirus

<400> SEQUENCE: 14
atttgcagta gacccagag                                               19

<210> SEQ ID NO 15
<211> LENGTH: 17
<212> TYPE: DNA
<213> ORGANISM: Human papillomavirus

<400> SEQUENCE: 15
gtgaaacccc tggcagt                                                 17

<210> SEQ ID NO 16
<211> LENGTH: 16
<212> TYPE: DNA
<213> ORGANISM: Human papillomavirus

<400> SEQUENCE: 16
tccggtaata ctgcag                                                  16

<210> SEQ ID NO 17
<211> LENGTH: 19
<212> TYPE: DNA
<213> ORGANISM: Human papillomavirus

<400> SEQUENCE: 17
tagtggaaat cgcacgtct                                               19

<210> SEQ ID NO 18
<211> LENGTH: 17
<212> TYPE: DNA
<213> ORGANISM: Human papillomavirus

<400> SEQUENCE: 18
tccggttcaa cagctac                                                 17

<210> SEQ ID NO 19
<211> LENGTH: 21
<212> TYPE: DNA
<213> ORGANISM: Human papillomavirus
<220> FEATURE:
<221> NAME/KEY: modified_base
<222> LOCATION: (3)..(3)
<223> OTHER INFORMATION: LNA residue
<220> FEATURE:
```

```
<221> NAME/KEY: modified_base
<222> LOCATION: (11)..(11)
<223> OTHER INFORMATION: LNA residue
<220> FEATURE:
<221> NAME/KEY: modified_base
<222> LOCATION: (16)..(16)
<223> OTHER INFORMATION: LNA residue

<400> SEQUENCE: 19
tgcctctatt caaagcagtg c                                              21

<210> SEQ ID NO 20
<211> LENGTH: 17
<212> TYPE: DNA
<213> ORGANISM: Human papillomavirus

<400> SEQUENCE: 20
gtaccactgg cacattg                                                   17

<210> SEQ ID NO 21
<211> LENGTH: 19
<212> TYPE: DNA
<213> ORGANISM: Human papillomavirus

<400> SEQUENCE: 21
atacacacag ctgccaggt                                                 19

<210> SEQ ID NO 22
<211> LENGTH: 16
<212> TYPE: DNA
<213> ORGANISM: Human papillomavirus

<400> SEQUENCE: 22
cttcacctgg cagctg                                                    16

<210> SEQ ID NO 23
<211> LENGTH: 15
<212> TYPE: DNA
<213> ORGANISM: Human papillomavirus

<400> SEQUENCE: 23
cactgtgcct caatc                                                     15

<210> SEQ ID NO 24

<400> SEQUENCE: 24

000

<210> SEQ ID NO 25
<211> LENGTH: 15
<212> TYPE: DNA
<213> ORGANISM: Human papillomavirus

<400> SEQUENCE: 25
acctggcagc tgtgt                                                     15

<210> SEQ ID NO 26
<211> LENGTH: 16
<212> TYPE: DNA
<213> ORGANISM: Human papillomavirus

<400> SEQUENCE: 26
tctaactctg gcaata                                                    16
```

<210> SEQ ID NO 27

<400> SEQUENCE: 27

000

<210> SEQ ID NO 28

<400> SEQUENCE: 28

000

<210> SEQ ID NO 29
<211> LENGTH: 26
<212> TYPE: DNA
<213> ORGANISM: Human papillomavirus

<400> SEQUENCE: 29
aggcgagaac aggtttttgc cagaca        26

<210> SEQ ID NO 30
<211> LENGTH: 19
<212> TYPE: DNA
<213> ORGANISM: Human papillomavirus

<400> SEQUENCE: 30
atcaacttcc tgaatcact        19

<210> SEQ ID NO 31
<211> LENGTH: 20
<212> TYPE: DNA
<213> ORGANISM: Human papillomavirus

<400> SEQUENCE: 31
aaggtactga catacgtgcc        20

<210> SEQ ID NO 32
<211> LENGTH: 18
<212> TYPE: DNA
<213> ORGANISM: Human papillomavirus

<400> SEQUENCE: 32
cacagatata cgtgcaaa        18

<210> SEQ ID NO 33

<400> SEQUENCE: 33

000

<210> SEQ ID NO 34
<211> LENGTH: 20
<212> TYPE: DNA
<213> ORGANISM: Human papillomavirus
<220> FEATURE:
<221> NAME/KEY: modified_base
<222> LOCATION: (5)..(5)
<223> OTHER INFORMATION: LNA residue
<220> FEATURE:
<221> NAME/KEY: modified_base
<222> LOCATION: (10)..(10)
<223> OTHER INFORMATION: LNA residue
<220> FEATURE:
<221> NAME/KEY: modified_base
<222> LOCATION: (13)..(13)
<223> OTHER INFORMATION: LNA residue
<220> FEATURE:

```
<221> NAME/KEY: modified_base
<222> LOCATION: (15)..(15)
<223> OTHER INFORMATION: LNA residue
<220> FEATURE:
<221> NAME/KEY: modified_base
<222> LOCATION: (18)..(18)
<223> OTHER INFORMATION: LNA residue

<400> SEQUENCE: 34
cacagatata cgtgcaaacc                                               20

<210> SEQ ID NO 35
<211> LENGTH: 16
<212> TYPE: DNA
<213> ORGANISM: Human papillomavirus

<400> SEQUENCE: 35
agtggtaatg gccgtg                                                   16

<210> SEQ ID NO 36

<400> SEQUENCE: 36

000

<210> SEQ ID NO 37
<211> LENGTH: 17
<212> TYPE: DNA
<213> ORGANISM: Human papillomavirus

<400> SEQUENCE: 37
tggtaatggc cgtgacc                                                  17

<210> SEQ ID NO 38
<211> LENGTH: 17
<212> TYPE: DNA
<213> ORGANISM: Human papillomavirus

<400> SEQUENCE: 38 cgtgaccccta tagaaag                                                 17

<210> SEQ ID NO 39
<211> LENGTH: 17
<212> TYPE: DNA
<213> ORGANISM: Human papillomavirus

<400> SEQUENCE: 39
tagcaatggt agagaac                                                  17

<210> SEQ ID NO 40

<400> SEQUENCE: 40

000

<210> SEQ ID NO 41
<211> LENGTH: 22
<212> TYPE: DNA
<213> ORGANISM: Human papillomavirus

<400> SEQUENCE: 41
atatttaaag ggtagcaatg gt                                            22

<210> SEQ ID NO 42
```

<400> SEQUENCE: 42

000

<210> SEQ ID NO 43

<400> SEQUENCE: 43

000

<210> SEQ ID NO 44
<211> LENGTH: 19
<212> TYPE: DNA
<213> ORGANISM: Human papillomavirus

<400> SEQUENCE: 44
ctgttggtga aaatgtacc                                                  19

<210> SEQ ID NO 45
<211> LENGTH: 20
<212> TYPE: DNA
<213> ORGANISM: Human papillomavirus

<400> SEQUENCE: 45
tgaaaatgta ccagacgatt                                                 20

<210> SEQ ID NO 46
<211> LENGTH: 16
<212> TYPE: DNA
<213> ORGANISM: Human papillomavirus

<400> SEQUENCE: 46
agccagttca aattat                                                     16

<210> SEQ ID NO 47
<211> LENGTH: 17
<212> TYPE: DNA
<213> ORGANISM: Human papillomavirus

<400> SEQUENCE: 47
tctattcaaa gcagtgc                                                    17

<210> SEQ ID NO 48
<211> LENGTH: 22
<212> TYPE: DNA
<213> ORGANISM: Human papillomavirus
<220> FEATURE:
<221> NAME/KEY: modified_base
<222> LOCATION: (5)..(5)
<223> OTHER INFORMATION: LNA residue
<220> FEATURE:
<221> NAME/KEY: modified_base
<222> LOCATION: (8)..(8)
<223> OTHER INFORMATION: LNA residue
<220> FEATURE:
<221> NAME/KEY: modified_base
<222> LOCATION: (11)..(11)
<223> OTHER INFORMATION: LNA residue
<220> FEATURE:
<221> NAME/KEY: modified_base
<222> LOCATION: (13)..(13)
<223> OTHER INFORMATION: LNA residue
<220> FEATURE:
<221> NAME/KEY: modified_base
<222> LOCATION: (15)..(15)
<223> OTHER INFORMATION: LNA residue
<220> FEATURE:
<221> NAME/KEY: modified_base
<222> LOCATION: (17)..(17)

```
<223> OTHER INFORMATION: LNA residue
<220> FEATURE:
<221> NAME/KEY: modified_base
<222> LOCATION: (20)..(20)
<223> OTHER INFORMATION: LNA residue

<400> SEQUENCE: 48
ctactgcctc tattcaaagc ag                                         22

<210> SEQ ID NO 49
<211> LENGTH: 21
<212> TYPE: DNA
<213> ORGANISM: Human papillomavirus

<400> SEQUENCE: 49
tgcctctatt caaagcagtg c                                          21

<210> SEQ ID NO 50
<211> LENGTH: 32
<212> TYPE: DNA
<213> ORGANISM: Human papillomavirus

<400> SEQUENCE: 50
ggaactactg cctctattca aagcagtgct gc                              32

<210> SEQ ID NO 51
<211> LENGTH: 22
<212> TYPE: DNA
<213> ORGANISM: Human papillomavirus

<400> SEQUENCE: 51
agaggctgtt cccgatgacc tg                                         22

<210> SEQ ID NO 52
<211> LENGTH: 26
<212> TYPE: DNA
<213> ORGANISM: Human papillomavirus

<400> SEQUENCE: 52
ttcccgatga cctgtacatt aaaggt                                     26

<210> SEQ ID NO 53

<400> SEQUENCE: 53

000

<210> SEQ ID NO 54

<400> SEQUENCE: 54

000

<210> SEQ ID NO 55
<211> LENGTH: 17
<212> TYPE: DNA
<213> ORGANISM: Human papillomavirus

<400> SEQUENCE: 55
ccagtgaacc ttatggg                                               17

<210> SEQ ID NO 56
<211> LENGTH: 17
<212> TYPE: DNA
<213> ORGANISM: Human papillomavirus
```

<400> SEQUENCE: 56
aaaacttggc gaggctg                                                     17

<210> SEQ ID NO 57
<211> LENGTH: 16
<212> TYPE: DNA
<213> ORGANISM: Human papillomavirus

<400> SEQUENCE: 57
aagggtccgg taatac                                                      16

<210> SEQ ID NO 58
<211> LENGTH: 19
<212> TYPE: DNA
<213> ORGANISM: Human papillomavirus

<400> SEQUENCE: 58
actgcagtta tccaaagta                                                   19

<210> SEQ ID NO 59
<211> LENGTH: 16
<212> TYPE: DNA
<213> ORGANISM: Human papillomavirus

<400> SEQUENCE: 59
atacacacaa ctgcca                                                      16

<210> SEQ ID NO 60

<400> SEQUENCE: 60

000

<210> SEQ ID NO 61
<211> LENGTH: 19
<212> TYPE: DNA
<213> ORGANISM: Human papillomavirus

<400> SEQUENCE: 61
aatacacaca actgccagg                                                   19

<210> SEQ ID NO 62
<211> LENGTH: 20
<212> TYPE: DNA
<213> ORGANISM: Human papillomavirus
<220> FEATURE:
<221> NAME/KEY: modified_base
<222> LOCATION: (3)..(3)
<223> OTHER INFORMATION: LNA residue
<220> FEATURE:
<221> NAME/KEY: modified_base
<222> LOCATION: (6)..(6)
<223> OTHER INFORMATION: LNA residue
<220> FEATURE:
<221> NAME/KEY: modified_base
<222> LOCATION: (9)..(9)
<223> OTHER INFORMATION: LNA residue
<220> FEATURE:
<221> NAME/KEY: modified_base
<222> LOCATION: (12)..(12)
<223> OTHER INFORMATION: LNA residue
<220> FEATURE:
<221> NAME/KEY: modified_base
<222> LOCATION: (15)..(15)
<223> OTHER INFORMATION: LNA residue

<400> SEQUENCE: 62
ctagcgctaa tatgcgtgaa                                                    20

<210> SEQ ID NO 63
<211> LENGTH: 22
<212> TYPE: DNA
<213> ORGANISM: Human papillomavirus

<400> SEQUENCE: 63
tgcgtgaaac ccctggcagt tg                                                 22

<210> SEQ ID NO 64
<211> LENGTH: 20
<212> TYPE: DNA
<213> ORGANISM: Human papillomavirus

<400> SEQUENCE: 64
acacagtacc tacggaccta                                                    20

<210> SEQ ID NO 65
<211> LENGTH: 18
<212> TYPE: DNA
<213> ORGANISM: Human papillomavirus

<400> SEQUENCE: 65
cgctaatatg cgtgaaac                                                      18

<210> SEQ ID NO 66
<211> LENGTH: 16
<212> TYPE: DNA
<213> ORGANISM: Human papillomavirus

<400> SEQUENCE: 66
taccactggc acattg                                                        16

<210> SEQ ID NO 67

<400> SEQUENCE: 67

000

<210> SEQ ID NO 68
<211> LENGTH: 16
<212> TYPE: DNA
<213> ORGANISM: Human papillomavirus

<400> SEQUENCE: 68
taccactggc acattg                                                        16

<210> SEQ ID NO 69

<400> SEQUENCE: 69

000

<210> SEQ ID NO 70
<211> LENGTH: 23
<212> TYPE: DNA
<213> ORGANISM: Human papillomavirus

<400> SEQUENCE: 70
tcaggcgcgg ttggtgaatc ggt                                                23

<210> SEQ ID NO 71

<210> SEQ ID NO 71
<211> LENGTH: 18
<212> TYPE: DNA
<213> ORGANISM: Human papillomavirus

<400> SEQUENCE: 71
ttcaacagct actttagc        18

<210> SEQ ID NO 72
<211> LENGTH: 17
<212> TYPE: DNA
<213> ORGANISM: Human papillomavirus

<400> SEQUENCE: 72
ctccggttca acagcta         17

<210> SEQ ID NO 73
<211> LENGTH: 22
<212> TYPE: DNA
<213> ORGANISM: Human papillomavirus

<400> SEQUENCE: 73
tgcctgatac tcttataatt aa   22

<210> SEQ ID NO 74
<211> LENGTH: 13
<212> TYPE: DNA
<213> ORGANISM: Human papillomavirus

<400> SEQUENCE: 74
accccgagcg gct             13

<210> SEQ ID NO 75
<211> LENGTH: 18
<212> TYPE: DNA
<213> ORGANISM: Human papillomavirus

<400> SEQUENCE: 75
tgttaacacc ccgagcgg        18

<210> SEQ ID NO 76

<400> SEQUENCE: 76

000

<210> SEQ ID NO 77
<211> LENGTH: 20
<212> TYPE: DNA
<213> ORGANISM: Human papillomavirus

<400> SEQUENCE: 77
aacagggctg gcgaggtggg      20

<210> SEQ ID NO 78
<211> LENGTH: 23
<212> TYPE: DNA
<213> ORGANISM: Human papillomavirus

<400> SEQUENCE: 78
tttaacaggg ctggcgaggt ggg  23

<210> SEQ ID NO 79
<211> LENGTH: 19
<212> TYPE: DNA

```
<213> ORGANISM: Human papillomavirus

<400> SEQUENCE: 79
acagggctgg cgaggtggg                                                   19

<210> SEQ ID NO 80
<211> LENGTH: 22
<212> TYPE: DNA
<213> ORGANISM: Human papillomavirus

<400> SEQUENCE: 80
tttttaacag ggctggcgag gt                                               22
```